United States Patent [19]

Bandman et al.

[11] Patent Number: 6,046,001
[45] Date of Patent: Apr. 4, 2000

[54] HUMAN FATTY ACID BETA-OXIDATION ENZYMES

[75] Inventors: Olga Bandman; Jennifer L. Hillman, both of Mountain View; Karl J. Guegler, Menlo Park; Neil C. Corley, Mountain View; Y. Tom Tang; Purvi Shah, both of Sunnyvale, all of Calif.

[73] Assignee: Incyte Pharmaceuticals, Inc., Palo Alto, Calif.

[21] Appl. No.: 09/002,298

[22] Filed: Dec. 31, 1997

[51] Int. Cl.[7] .............................. C12Q 1/68; C12N 9/02; C12N 15/00; C07H 21/04

[52] U.S. Cl. ........................... 435/6; 435/189; 435/252.3; 435/254.11; 435/320.1; 435/325; 536/23.2

[58] Field of Search ........................... 536/23.2; 435/194, 435/189, 320.1, 252.3, 325, 254.11, 6

[56] References Cited

PUBLICATIONS

Eaton, S. et al., "Mammalian mitochondrial β–oxidation", *Biochem. J.*, 320: 345–357 (1996).
Mannaerts, G.P. and P.P. van Veldhoven, "Metabolic pathways in mammalian peroxisomes", *Biochimie*, 75: 147–158 (1993).
Koivuranta, K.T. et al., "Isolation and characterization of cDNA for human 120 kDa mitochondrial 2,4–dienoyl–coenzyme A reductase", *Biochem. J.*, 304: 787–792 (1994) (GI 602703).
Smeland, T.E. et al., "NADPH–dependent β–oxidation of unsaturated fatty acids with double bonds extending from odd–numbered carbon atoms", *Proc. Natl. Acad. Sci. USA*, 89: 6673–6677 (1992).
Dommes, V. et al., "Degradation of Unsaturated Fatty Acids in Peroxisomes —Existence of a 2,4–Dienoyl–CoA Reductase Pathway", *J. Biol. Chem.*, 256: 8259–8262 (1981).
Hakkola, E.H. and J.K. Hiltunen, "The existence of two mitochondrial isoforms of 2,4–dienoyl–CoA reductase in the rat", *Eur. J. Biochem.*, 215: 199–204 (1993).
Hirose, A. et al., "cDNA cloning of rat liver 2, 4–dienoyl–CoA reductase", *Biochim. Biophys. Acta*, 1049: 346–349 (1990) (GI 111287).
Coe, J.G.S. et al., "Identification of a sporulation–specific promoter regulating divergent trascription of two sporulation genes in *Saccharomyces cerevisiae*", *Mol. Gen. Genet.*, 244: 661–672 (1994) (GI 730864).
Guritz, A. et al., "The *Saccharomyces cerevisiae* Peroxisomal 2, 4–Deinoyl–CoA Reductase Is Encoded by the Oleate–inducible Gene SPS19", *J. Biol. Chem.*, 272: 22140–22147 (1997).
Engel, C. K. et al., "Crystal structure of enoyl–coenzyme A CoA) hydratase at 2.5 Å resolution: a spiral fold defines the CoA–binding pocket", *EMBO J.*, 15: 5135–5145 (1996).
Kanazawa, M. et al., "Molecular Cloning and Sequence Analysis of the cDNA for Human Mitochondrial Short–Chain Enoyl–CoA Hydratase", *Enzyme Protein*, 47: 9–13 (1993).

Janssen, U. et al., "Human Mitochndrial Enoyl–CoA Hydratase Gene (ECHS1): Structural Organization and Assignment to Chromosome 10q26.2–q26.3", *Genomics*, 40: 470–475 (1997) (GI 1922287).
FitzPatrick, D.R. et al., "Isolation and Characterization of Rat and Human cDNAs Encoding a Novel Putative Peroxisomal Enoyl–CoA Hydratase", *Genomics*, 27: 457–466 (1995) (GI 564065).
Hoefler, G. et al., "cDNA Cloning of the Human Peroxisomal Enoyl–CoA Hydratase: 3–Hydroxyacyl–CoA Dehydrogenase Bifunctional Enzyme and Localization to Chromosome 3q26.3–3q28: A Free Left Alu Arm Is Inserted in the 3' Noncoding Region", *Genomics*, 19: 60–67 (1994).
Nakagawa, J. et al., "AUH, a gene encoding an Au–specific RNA binding protein with intrinsic enoyl–CoA hydratase activity", *Proc. Natl. Acad. Sci. USA*, 92: 2051–2055 (1995) (GI 780241).
Wu, W. et al., "Structure of Hexadienoyl–CoA Bound to Enoyl–CoA Hydratase Determined by Transferred Nuclear Overhauser Effect Measurements: Mechanistic Predictions Based on the X–ray Structure of 4–(Chlorobenzoyl)–CoA Dehalogenase" *Biochemistry*, 36: 2211–2220* (1997).
Roe, C.R. et al., "2,4–Dienoyl–Coenzyme A Reductase Deficiency: A Possible New Disorder of Fatty Acid Oxidation", *J. Clin. Invest.*, 85: 1703–1707 (1990).
Cotran, R.S. et al., *Robbins Pathologic Basis of Disease*, W.B. Saunders Co., Philadelphia, PA, p. 866 (1994).
Egidio, R.J. et al., "Medium–Chain Acyl–CoA Dehydrogenase Deficiency", *Am. Fam. Physician*, 39: 221–226 (1989).
Suzuki, Y. et al., "Novel Subtype of Peroxisomal Acyl–CoA Oxidase Deficiency and Bifunctional Enzyme Deficiency with Detectable Enzyme Protein: Identification by Means of Complementation Analysis", *Am. J. Hum. Genet.*, 54: 36–43 (1994).
Watkins, P.A. et al., "Peroxisomal Bifunctional Enzyme Deficiency" *J. Clin. Invest.*, 83: 771–777 (1989).
el Bouhtoury, F. et al., "Peroxisomal Enzymes in Normal and Tumoral Human Breast", *J. Pathol.*, 166: 27–35 (1992).
Cable, S. et al., "Peroxisomes in human colon carcinomas—A cytochemical and biochemical study", *Virchows Arch. B Cell Pathol.*, 62: 221–226 (1992).
Jonniaux, J.L. et al., (Direct Submission), GenBank Sequence Database (Accession 730864), National Center for Biotechnology Information, National Library of Medicine, Bethesda, Maryland, 20894, (GI 730864).
Jonniaux, J.L. et al., (Direct Submission), GenBank Sequence Database (Accession X78898), National Center for Biotechnology Information, National Library of Medicine, Bethesda, Maryland, 20894, (GI 600045).

(List continued on next page.)

*Primary Examiner*—Bradley Sisson
*Assistant Examiner*—Einar Stole
*Attorney, Agent, or Firm*—Susan K. Sather; Incyte Pharmaceuticals, Inc.

[57] ABSTRACT

The invention provides human fatty acid beta-oxidation enzymes (HUFA) and polynucleotides which identify and encode HUFA. The invention also provides expression vectors, host cells, antibodies, agonists, and antagonists. The invention also provides methods for treating or preventing disorders associated with expression of HUFA.

11 Claims, 18 Drawing Sheets

OTHER PUBLICATIONS

Jonniaux, J.L. et al., "A 21•7 kb DNA Segment on the Left Arm of Yeast Chromosome XIV Carries WH13, GCR2, SPX18, SPX19, an Homologue to the Heat Shock Gene SSB1 and 8 New Open Reading Frames of Unknown Function", *Yeast,* 10: 1639–1645 (1994) (GI 600045).

Koivuranta, K.T. et al., (Direct Submission), GenBank Sequence Database (Accession L26050), National Center for Biotechnology Information, National Library of Medicine, Bethesda, Maryland, 20894, (GI 602702).

Hirose, A. et al., (Direct Submission), GenBank Sequence Database (Accession 111287), National Center for Biotechnology Information, National Library of Medicine, Bethesda, Maryland, 20894, (GI 111287).

Hirose, A. et al., (Direct Submission), GenBank Sequence Database (Accession D00569), National Center for Biotechnology Information, National Library of Medicine, Bethesda, Maryland, 20894, (GI 220731).

Nakagawa, J. et al., (Direct Submission), GenBank Sequence Database (Accession X79888), National Center for Biotechnology Information, National Library of Medicine, Bethesda, Maryland, 20894, (GI 780240).

Janssen, U. et al., (Direct Submission), GenBank Sequence Database (Accession X98126), National Center for Biotechnology Information, National Library of Medicine, Bethesda, Maryland, 20894, (GI 1922286)*.

Fitzpatrick, D.R. et al., (Direct Submission), GenBank Sequence Database (Accession U16660), National Center for Biotechnology Information, National Library of Medicine, Bethesda, Maryland, 20894, (GI 564064).

Nada, M.A. et al., "Spectrophotometric Assay of 2,4–Dienoyl Coenzyme A Reductase with 5–Phenyl–2,4–pentadienoyl–Coenzyme A as Substrate", *Lipids,* 29: 517–521 (1994).

Wanders, R.J.A. et al., "Human Trifunctional Protein Deficiency: A New Disorder of Mitochondrial Fatty Acid β–Oxidation", *Biochem. Biophys. Res. Comm.,* 188: 1139–1145 (1992).

Sigma Catalog (1995). Sigma Chemical Co., St. Louis, MO., 1995.

Harper's Biochemistry (1993) Eds. Murray et al. 23rd Edition. Appleton & Lange, Norwalk, CT. p. 420, 1993.

```
                                                                 54
5' NNC CTG AGA CCC AGA AGG GCC TGC GCT CAG CTG CTC TGG CAC CCC GCT GCA GGG 9      18       27      36      45      54                108
ATG GCC TCC TGG GCT AAG GGC AGG AGC TAC CTG GCG CCT GGT TTG CAG GGC
 M   A   S   W   A   K   G   R   S   Y   L   A   P   G   L   Q   G 63      72       81      90      99                        162
CAA GTG GCC ATC GTC ACC GGC GCC ACG GGC ATC GGA AAA GCC ATC GTG AAG
 Q   V   A   I   V   T   G   A   T   G   I   G   K   A   I   V   K 117     126      135     144     153                        216
GAG CTC CTG GAG CTG GGG AGT AAT GTG GTC ATT GCA TCC CGT AAG TTG GAG AGA
 E   L   L   E   L   G   S   N   V   V   I   A   S   R   K   L   E   R 171     180      189     198     207                        270
TTG AAG TCT GCG GCA GAT GAA CTG CAG GCC AAC CTA CCT CCC ACA AAG CAG GCA
 L   K   S   A   A   D   E   L   Q   A   N   L   P   P   T   K   Q   A 225     234      243     252     261                        324
CGA GTC ATT CCC ATA CAA TGC AAC ATC CGG AAT GAG GAG GAG GTG AAT AAT TTG
 R   V   I   P   I   Q   C   N   I   R   N   E   E   E   V   N   N   L 279     288      297     306     315                        378
GTC AAA TCT ACC TTA GAT ACT TTT GGT AAG ATC AAT TTC TTG GTG AAC AAT GGA
 V   K   S   T   L   D   T   F   G   K   I   N   F   L   V   N   N   G 333     342      351     360     369
```

FIGURE 1A

```
      387             396       405             414             423             432
GGA GGC CAG TTT CTT TCC CCT GCT GAA CAC ATC AGT TCT AAG GGA TGG CAC GCT
 G   G   Q   F   L   S   P   A   E   H   I   S   S   K   G   W   H   A 441             450       459             468             477             486
GTG CTT GAG ACC AAC CTG ACG GGT ACC TTC TAC ATG TGC AAA GCA GTT TAC AGC
 V   L   E   T   N   L   T   G   T   F   Y   M   C   K   A   V   Y   S 495             504       513             522             531             540
TCC TGG ATG AAA GAG CAT GGA GGA TCT ATC ATC GTC AAT ATC ATT GTC CCT ACT AAA
 S   W   M   K   E   H   G   G   S   I   I   V   N   I   I   V   P   T   K 549             558       567             576             585             594
GCT GAA TTT CCA TTA GCT GTG CAT TCT GGA TCT GCA AGA GCA GGT GTT TAC AAC
 A   G   F   P   L   A   V   H   S   G   A   R   A   G   V   Y   N 603             612       621             630             639             648
CTC ACC AAA TCT TTA GCT TTG GAA TGG GCC TGC AGT GGA ATA CGG ATC AAT TGT
 L   T   K   S   L   A   L   E   W   A   C   S   G   I   R   I   N   C 657             666       675             684             693             702
GTT GCC CCT GGA GTT ATT TAT TCC CAG ACT GCT GTG GAG AAC TAT GGT TCC TGG
 V   A   P   G   V   I   Y   S   Q   T   A   V   E   N   Y   G   S   W 711             720       729             738             747             756
GGA CAA AGC TTC TTT GAA GGG TCT TTT CAG AAA ATC CCC GCT AAA CGA ATT GGT
 G   Q   S   F   F   E   G   S   F   Q   K   I   P   A   K   R   I   G
```

FIGURE 1B

```
                765            774  783      792          801          810
GTT CCT GAG GAG GTC TCC TCT GTG GTC TGC TTC CTA CTG TCT CCT GCA GCT TCC
 V   P   E   E   V   S   S   V   V   C   F   L   L   S   P   A   A   S 819            828          837          846          855          864
TTC ATC ACT GGA CAG TCG GTG GAT GGG GGC CGG AGT CTC TAT ACT CAC
 F   I   T   G   Q   S   V   D   G   G   R   S   L   Y   T   H 873            882          891          900          909          918
TCG TAT GAG GTA CCA GAT CAT GAC AAC TGG CCC AAG GGA GCA GGG GAC CTT TCT
 S   Y   E   V   P   D   H   D   N   W   P   K   G   A   G   D   L   S 927            936          945          954          963          972
GTT GTC AAA AAG ATG AAG GAG ACC TTT AAG GAG AAA GCT AAG CTC TGA GCT GAG
 V   V   K   K   M   K   E   T   F   K   E   K   A   K   L   *

981            990          999          1008         1017         1026
GAA ACA AGG TGT CCT CCA TCC CCC AGT GCC TTC ACA TCT TGA GGA TAT GCT TCT 1035           1044         1053         1062         1071         1080
GTA CTT TTT AAA AGC TTA TAG TTG GTA TGG AAA ACA TTT TTC TTA TTT TTA AGT 1089           1098         1107         1116         1125         1134
GTT ATT AAT TAT ATC TAT GGA AAA ACT ATT CCT GAA ATA TAT ACA GTC TTA TGT
```

FIGURE 1C

```
      1143         1152         1161         1170         1179         1188
CGC AAT CAG AGT CTT TTA ACC TAT GAT TTA AGA ATG TAT AAG TAA CAG AGA TTA 1197         1206
ACA TAT TTT AAT GAC TTT ACT C 3'
```

FIGURE 1D

```
         9          18          27          36          45          54
5' NAA GCA CTT CCT GTC TGC GGC ATA CAA AAT GTA TGG CAC GGA ATT TTA AGC TTA 63          72          81          90          99         108
CTG AGC TTT ATA AAC ACG TCA CAT TCA CAC ATT CAA GAC ACA CAC TGG ATA TTC 117         126         135         144         153         162
GGA TAA AAA CAA ACA AAC AAA AAA CAG GCT AAA TAC CCA TTC CCC TCA ATA ACT 171         180         189         198         207         216
TGG ATA AGA TAC CTA AAA AAG GTC GAC TTC GGT ACC TTT CTG TCT TCT CCC CTC 225         234         243         252         261         270
TCG CTA TTT GCC TAC ACT GGC TTC CTC ACC TCC ACT TTT TCT CAC GTT TAT CTG 279         288         297         306         315         324
AGC GAA AAC AAG CAC GGT TCG GCA GCC TCC TTT CCC AGC CCT ACC TTT GTG CTG 333         342         351         360         369         378
CAA AAG CGA AAA TTC AAA AGC CAA GTA CAA TAG GAG ACC GCC CAC CCT GGC TCC

FIGURE 2A
```

```
        387                396         405         414         423         432
CTC GTG ACA CGA GGG AGC GCG AAG CGG AGG GCG CCT CGC GGC AGG AGC GGG ATT 441                450         459         468         477         486
TCC GGG GTC ACG GGA ACC GGC AGG ACG GGA ACG GGA TAA AGT TCC TGG AGA AAG GAA 495                504         513         522         531         540
AGG AGA GCG TGG GAT AGT AAA AGA GAA GAC GCG GAG AAG AGG AGA GGA CCT ACA 549                558         567         576         585         594
AGA ACG GAG GAC AGG GGC GCA CGA TGG TCC CGG GAG CGG GAG AAA CAA AGG CAC 603                612         621         630         639         648
GCA AAA CGG AAA AGC GTG TGT AGG GGA GCG GAA AAG GAA GTC ACC ACC GTG GCC 657                666         675         684         693         702
TGC GAC GAA ATG GCG AAA AGT CTT TTG AAG ACA GCC TCT CTG TCT GGA AGG ACA
            M   A   K   S   L   L   K   T   A   S   L   S   G   R   T 711                720         729         738         747         756
AAA TTG CTA CAT CAA ACA GGA TTG TCA CTT TAT AGT ACA TCC CAT GGA TTT TAT
 K   L   H   Q   T   G   L   S   L   Y   S   T   S   H   G   F   Y
```

FIGURE 2B

```
765         774         783         792         801         810
GAG GAA GTG AAA ACA CTT CAG CAG TTT CCT GGT GGA TCC ATT GAC CTT
 E   E   V   K   T   L   Q   Q   F   P   G   G   S   I   D   L 819         828         837         846         855         864
CAG AAG GAA GAC AAT GGC ATT CTT ACT CTG AAC AAT CCA AGT AGA ATG
 Q   K   E   D   N   G   I   L   T   L   N   N   P   S   R   M 873         882         891         900         909         918
AAT GCC TTT TCA GGT GTT ATG ATG CTA CAA CTT CTG GAA AAA GTA ATT GAA TTG
 N   A   F   S   G   V   M   M   L   Q   L   L   E   K   V   I   E   L 927         936         945         954         963         972
GAA AAT TGG ACA GAG GGG AAA GGC CTC ATT GTC CGT GGG GCA AAA AAT ACT TTC
 E   N   W   T   E   G   K   G   L   I   V   R   G   A   K   N   T   F 981         990         999         1008        1017        1026
TCT TCA GGA TCT GAT CTG AAT GCT GTG AAA TCA CTA GGA ACT CCA GAG GAT GGA
 S   S   G   S   D   L   N   A   V   K   S   L   G   T   P   E   D   G 1035        1044        1053        1062        1071        1080
ATG GCC GTA TGC ATG TTC ATG CAA AAC ACC TTA ACA AGA TTT ATG AGA CTT CCT
 M   A   V   C   M   F   M   Q   N   T   L   T   R   F   M   R   L   P 1089        1098        1107        1116        1125        1134
TTA ATA AGT GTT GCG CTG GTT CAA GGT TGG GCA TTG GGT GGA GCA GAA TTT
 L   I   S   V   A   L   V   Q   G   W   A   L   G   G   A   E   F
```

FIGURE 2C

```
       1143            1152            1161            1170            1179            1188
ACT ACA GCA TGT GAT TTC AGG TTA ATG ACT CCA GAG AGT AAG ATC AGA TTC GTC
 T   T   A   C   D   F   R   L   M   T   P   E   S   K   I   R   F   V 1197            1206            1215            1224            1233            1242
CAC AAA GAG ATG GGC ATA ATA CCA AGC TGG GGT GGC ACC ACC CGG CTA GTT GAA
 H   K   E   M   G   I   I   P   S   W   G   G   T   T   R   L   V   E 1251            1260            1269            1278            1287            1296
ATA ATC GGA AGT AGA CAA GCT CTC AAA GTG TTG AGT GGG GCC CTT AAA CTG GAT
 I   I   G   S   R   Q   A   L   K   V   L   S   G   A   L   K   L   D 1305            1314            1323            1332            1341            1350
TCA AAA AAT GCT CTA AAC ATA GGA ATG GTT GAA GAG GTC TTG CAG TCT TCA GAT
 S   K   N   A   L   N   I   G   M   V   E   E   V   L   Q   S   S   D 1359            1368            1377            1386            1395            1404
GAA ACT AAA TCT CTA GAA GAG GCA CAA GAA TGG CTA AAG CAA TTC ATC CAA GGG
 E   T   K   S   L   E   E   A   Q   E   W   L   K   Q   F   I   Q   G 1413            1422            1431            1440            1449            1458
CCA CCG GAA GTA ATT AGA GCT TTG AAA AAA TCT GTT TGT TCA GGC AGA GAG CTA
 P   P   E   V   I   R   A   L   K   K   S   V   C   S   G   R   E   L 1467            1476            1485            1494            1503            1512
TAT TTG GAG GAA GCA TTA CAG AAC GAA AGA GAT CTT TTA GGA ACA GTT TGG GGT
 Y   L   E   E   A   L   Q   N   E   R   D   L   L   G   T   V   W   G

FIGURE 2D
```

```
     1521        1530        1539        1548        1557       1566
GGG CCT GCA AAT TTA GAG GCT ATT GCT AAG AAA GGA AAA TTT AAT AAA TAA TTG
 G   P   A   N   L   E   A   I   A   K   K   G   K   F   N   K   *

1575        1584        1593        1602        1611       1620
GTT TTT CGT GTG GAT GTA CTC CAA GTA CTC CAG TGA CTA ATA TGT ATA AAT 1629        1638        1647        1656        1665       1674
GTT AAA TGA TAT TAA ATA TGA ACA TCA GAA TTA CTT TGA AGG CTA CTA ATA 1683        1692        1701        1710        1719       1728
TGC AGA CTT ACT TTT AAT CAT TTG AAT ATC TGA ACT CAT TTA CCT CAT TTC TTG 1737        1746        1755        1764        1773       1782
CCA ATT ACT CAC TTG GGT ATT TAC TGC GTA ATC TGG AAC ATT TAG CTA AAA TAT 1791        1800        1809        1818        1827       1836
ACA CTT TTG GCT TAA AAA TTA TTG CTG TCA ATT CCA ATA ATA ATT CTT AGC TTA 1845        1854        1863        1872        1881       1890
TAA CCA AAG AGC AGT GTT TAA AAG GAG AGC TTC TAT ACA AAA CCT ATT CCT GGC
```

FIGURE 2E

```
                1899      1908      1917      1926      1935      1944
                GTT ACT TTT CAT ACA ATT TTT GTT CTG TTT TAC CTG GAA ATA ATT TAC CAA AAT 1953      1962      1971      1980      1989      1998
                AAC TGA GTG TTG CTG CTA AAG AAC AAA AGT GGG GAG GTA TCA GGG AAC AAG AAA 2007      2016      2025      2034      2043      2052
                ACA AGA AAG GGT ATG ATC AAT CAT TTT CTT CTG CTC CAA ACA GCT GGA GTA AAA 2061      2070      2079      2088      2097      2106
                TTC ATG GGA AAT GGC CCT TCA TTT AAA AAA AGA TGT ACC TCA CTA CCC ACT ACA 2115      2124      2133      2142      2151      2160
                AAT TTG GAA CTT TGT TCT TTT CAA TAA TTA GTT TTC TAT TGT AAA TTA CCT ACT 2169      2178      2187      2196      2205      2214
                AAA CAG TGG TAG CCA TGA CAT GGA AAG TCA ACT GAT TCT ACA ATT GGA CAT TCA 2223      2232      2241      2250      2259      2268
                TTT GTG TGC CCT GGA ATT TCC AAC TAG TAA TAA ACA ACT ACT GTT GAT GTA GTT
```

FIGURE 2F

```
      2277        2286        2295        2304        2313        2322
TTA AAC CAC TTG AAG GGA CTC ATG AAG CAT CCT GCA ACA TAA ATT TGC ATT TTT 2331        2340        2349        2358        2367        2376
ACA TCA GAT TTC TTT TTC CTG AAA AAC TAA CCT TCT AAC AAC TAT CTT 2385        2394        2403        2412        2421        2430
TCA AAA GTA AAT GTA ATA AAA ATG CAC AAC ATA AAA TGT TTA TGA TCC CAG CAA 2439        2448        2457        2466        2475        2484
TAC ACT TTT TAA AAA ATG TGA AAG TCA AAG AAT TAA GTT CTA GTT CTG ACT CAT 2493        2502        2511        2520        2529        2538
CAC AAG AGG TCA AAA GTA TTT GCT ACT GTA ACA TTC AAT TCA CAT TTG AGA ATC 2547        2556        2565        2574        2583        2592
ATG GTA AAA ATA ACT TGT ATT TGC CTT ACC ATC ATG ATC CTA CTG TTG AGT TAG 2601        2610        2619        2628        2637        2646
GAA AAT ATG GTT AGA CAG ACT CAC ATT ACT TTT TTT CAG AGG TAA ACT CTA GAT
```

FIGURE 2G

```
     2655      2664          2673      2682          2691      2700
TAC TGT GTC AAC CCA ATA CTA TTT GGC CAT AGA TGT AAA AAC TAC CAA ATA AAA
2709
GTG GAT TTT GTG TC 3'
```

HUMAN FATTY ACID BETA-OXIDATION ENZYMES

FIELD OF THE INVENTION

This invention relates to nucleic acid and amino acid sequences of human fatty acid beta-oxidation enzymes and to the use of these sequences in the diagnosis, treatment, and prevention of genetic disorders, neuronal disorders, cancer, infectious diseases, liver disorders, and cardiac and skeletal muscle disorders.

BACKGROUND OF THE INVENTION

Mitochondrial and peroxisomal beta-oxidation enzymes degrade saturated and unsaturated fatty acids by sequential removal of two-carbon units from Coenzyme A (CoA)-activated fatty acids. The main beta-oxidation pathway degrades both saturated and unsaturated fatty acids while the auxiliary pathway performs additional steps required for the degradation of unsaturated fatty acids.

The pathways of mitchondrial and peroxisomal beta-oxidation use similar enzymes, but have different substrate specificities and functions. Mitochondria oxidize short-, medium-, and long-chain fatty acids to produce energy for cells. Mitochondrial beta-oxidation is a major energy source for cardiac and skeletal muscle. In liver, it provides ketone bodies to the peripheral circulation when glucose levels are low as in starvation, endurance exercise, and diabetes. (Eaton, S. et al. (1996) Biochem. J. 320:345–357.) Peroxisomes oxidize medium-, long-, and very-long-chain fatty acids, dicarboxylic fatty acids, branched fatty acids, prostaglandins, xenobiotics, and bile acid intermediates. The chief roles of peroxisomal beta-oxidation are to shorten toxic lipophilic carboxylic acids to facilitate their excretion and to shorten very-long-chain fatty acids prior to mitochondrial beta-oxidation. (Mannaerts, G. P. and Van Veldhoven, P. P. (1993) Biochimie 75:147–158.)

The auxiliary beta-oxidation enzyme 2,4-dienoyl-CoA reductase catalyzes the following reaction:

This reaction removes even-numbered double bonds from unsaturated fatty acids prior to their entry into the main beta-oxidation pathway. (Koivuranta, K. T. et al. (1994) Biochem. J. 304:787–792.) The enzyme may also remove odd-numbered double bonds from unsaturated fatty acids. (Smeland, T. E. et al. (1992) Proc. Natl. Acad. Sci. USA 89:6673–6677.)

Rat 2,4-dienoyl-CoA reductase is located in both mitochondria and peroxisomes. (Dommes, V. et al. (1981) J. Biol. Chem. 256:8259–8262.) Two immunologically different forms of rat mitochondrial enzyme exist with molecular masses of 60 kDa and 120 kDa. (Hakkola, E. H. and Hiltunen, J. K. (1993) Eur. J. Biochem. 215:199–204.) The 120 kDa mitochondrial rat enzyme is synthesized as a 335 amino acid precursor with a 29 amino acid N-terminal leader peptide which is cleaved to form the mature enzyme. (Hirose, A. et al. (1990) Biochim. Biophys. Acta 1049:346–349.) A human mitochondrial enzyme 83% similar to rat enzyme is synthesized as a 335 amino acid residue precursor with a 19 amino acid N-terminal leader peptide. (Koivuranta, supra.) These cloned human and rat mitochondrial enzymes function as homotetramers. (Koivuranta, supra.) A Saccharomyces cerevisiae peroxisomal 2,4-dienoyl-CoA reductase is 295 amino acids long, contains a C-terminal peroxisomal targeting signal, and functions as a homodimer. (Coe, J. G. S. et al. (1994) Mol. Gen. Genet. 244:661–672; and Gurvitz, A. et al. (1997) J. Biol. Chem. 272:22140–22147.) All 2,4-dienoyl-CoA reductases have a fairly well conserved NADPH binding site motif of sequence -h-X-h-X-Gly-X-Gly-X-X-Gly-X-X-X-h-X-X-h-. . . Asp/Glu-, where h=hydrophobic amino acid residue and X=any amino acid residue. (Koivuranta, supra.)

The main pathway beta-oxidation enzyme enoyl-CoA hydratase catalyzes the following reaction:

This reaction hydrates the double bond between C-2 and C-3 of 2-trans-enoyl-CoA, which is generated from saturated and unsaturated fatty acids. (Engel, C. K. et al. (1996) EMBO J. 15:5135–5145.) This step is downstream from the step catalyzed by 2,4-dienoyl-reductase. Different enoyl-CoA hydratases act on short-, medium-, and long-chain fatty acids. (Eaton, supra.) Mitochondrial and peroxisomal enoyl-CoA hydratases occur as both mono-functional enzymes and as part of multi-functional enzyme complexes. Human liver mitochondrial short-chain enoyl-CoA hydratase is synthesized as a 290 amino acid precursor with a 29 amino acid N-terminal leader peptide. (Kanazawa, M. et al. (1993) Enzyme Protein 47:9–13; and Janssen, U. et al. (1997) Genomics 40:470–475.) Rat short-chain enoyl-CoA hydratase is 87% identical to the human sequence in the mature region of the protein and functions as a homohexamer. (Kanazawa, supra; and Engel, supra) A mitochondrial trifunctional protein exists that has long-chain enoyl-CoA hydratase, 3-hydroxyacyl-CoA dehydrogenase, and long-chain 3-oxothiolase activities. (Eaton, supra.) In human peroxisomes, enoyl-CoA hydratase activity is found in both a 327 amino acid residue mono-functional enzyme and as part of a multi-functional enzyme, also known as bifunctional enzyme, which possesses enoyl-CoA hydratase, enoyl-CoA isomerase, and 3-hydroxyacyl-CoA hydrogenase activities. (FitzPatrick, D. R. et al. (1995) Genomics 27:457–466; and Hoefler, G. et al. (1994) Genomics 19:60–67.) A 339 amino acid residue human protein with short-chain enoyl-CoA hydratase activity also acts as an AU-specific RNA binding protein. (Nakagawa, J. et al. (1995) Proc. Natl. Acad. Sci. USA 92:2051–2055.) All enoyl-CoA hydratases share homology near two active site glutamic acid residues, with 17 amino acid residues highly conserved. (Wu, W.-J. et al. (1997) Biochemistry 36:2211–2220.)

Inherited deficiencies in mitochondrial and peroxisomal beta-oxidation enzymes are associated with severe diseases, some of which manifest themselves soon after birth and lead to death within a few years. Mitochondrial beta-oxidation associated deficiencies include, e.g., carnitine palmitoyl transferase and carnitine deficiency, very-long-chain acyl-CoA dehydrogenase deficiency, medium-chain acyl-CoA dehydrogenase deficiency, short-chain acyl-CoA dehydrogenase deficiency, electron transport flavoprotein and electron transport flavoprotein:ubiquinone oxidoreductase deficiency, trifunctional protein deficiency, and short-chain 3-hydroxyacyl-CoA dehydrogenase deficiency. (Eaton, supra.) Mitochondrial trifunctional protein (including enoyl-CoA hydratase) deficient patients have reduced long-chain enoyl-CoA hydratase activities and suffer from non-ketotic hypoglycemia, sudden infant death syndrome, cardiomyopathy, hepatic dysfunction, and muscle weakness, and may die at an early age. (Eaton, supra.) A patient with a deficiency in mitochondrial 2,4-dienoyl-CoA reductase was hypotonic soon after birth, had feeding difficulties, and died at four months from respiratory acidosis. (Roe, C. R. et al. (1990) J. Clin. Invest. 85:1703–1707.)

Defects in mitochondrial beta-oxidation are associated with Reye's syndrome, a disease characterized by hepatic dysfunction and encephalopathy that sometimes follows viral infection in children. Reye's syndrome patients may have elevated serum levels of free fatty acids. (Cotran, R. S. et al. (1994) *Robbins Pathologic Basis of Disease*, W. B. Saunders Co., Philadelphia, Pa., p.866.) Patients with mitochondrial short-chain 3-hydroxyacyl-CoA dehydrogenase deficiency and medium-chain 3-hydroxyacyl-CoA dehydrogenase deficiency also exhibit Reye-like illnesses. (Eaton, supra; and Egidio, R. J. et al. (1989) Am. Fam. Physician 39:221–226.)

Inherited conditions associated with peroxisomal beta-oxidation include Zellweger syndrome, neonatal adrenoleukodystrophy, infantile Refsum's disease, acyl-CoA oxidase deficiency, peroxisomal thiolase deficiency, and bifunctional protein deficiency. (Suzuki, Y. et al. (1994) Am. J. Hum. Genet. 54:36–43; Hoefler, supra) Patients with peroxisomal bifunctional enzyme, including enoyl-CoA hydratase, deficiency suffer from hypotonia, seizures, psychomotor defects, and defective neuronal migration; accumulate very-long-chain fatty acids; and typically die within a few years of birth. (Watkins, P. A. et al. (1989) J. Clin. Invest. 83:771–777.)

Peroxisomal beta-oxidation is impaired in cancerous tissue. Although neoplastic human breast epithelial cells have the same number of peroxisomes as do normal cells, fatty acyl-CoA oxidase activity is lower than in control tissue. (el Bouhtoury, F., et al. (1992) J. Pathol. 166:27–35.) Human colon carcinomas have fewer peroxisomes than normal colon tissue and have lower fatty-acyl-CoA oxidase and bifunctional enzyme (including enoyl-CoA hydratase) activities than normal tissue. (Cable, S., et al. (1992) Virchows Arch. B Cell Pathol. Incl. Mol. Pathol. 62:221–226.)

The discovery of new human fatty acid beta-oxidation enzymes and the polynucleotides encoding them satisfies a need in the art by providing new compositions which are useful in the diagnosis, treatment, and prevention of genetic disorders, neuronal disorders, cancer, infectious diseases, liver disorders, and cardiac and skeletal muscle disorders.

SUMMARY OF THE INVENTION

The invention features substantially purified polypeptides, human fatty acid beta-oxidation enzymes, referred to collectively as "HUFA" and individually as "HUFA-1 " and "HUFA-2." In one aspect, the invention provides a substantially purified polypeptide, HUFA, comprising an amino acid sequence selected from the group consisting of SEQ ID NO: 1, SEQ ID NO:3, a fragment of SEQ ID NO: 1, and a fragment of SEQ ID NO:3.

The invention further provides a substantially purified variant of HUFA having at least 90% amino acid identity to the amino acid sequences of SEQ ID NO: 1 or SEQ ID NO:3, or to a fragment of either of these sequences. The invention also provides an isolated and purified polynucleotide sequence encoding the polypeptide comprising an amino acid sequence selected from the group consisting of SEQ ID NO: 1, SEQ ID NO:3, a fragment of SEQ ID NO: 1, and a fragment of SEQ ID NO:3. The invention also includes an isolated and purified polynucleotide variant having at least 90% polynucleotide identity to the polynucleotide sequence encoding the polypeptide comprising an amino acid sequence selected from the group consisting of SEQ ID NO: 1, SEQ ID NO:3, a fragment of SEQ ID NO:1, and a fragment of SEQ ID NO:3.

Additionally, the invention provides a composition comprising a polynucleotide sequence encoding the polypeptide comprising the amino acid sequence selected from the group consisting of SEQ ID NO:1, SEQ ID NO:3, a fragment of SEQ ID NO:1, and a fragment of SEQ ID NO:3. The invention further provides an isolated and purified polynucleotide sequence which hybridizes under stringent conditions to the polynucleotide sequence encoding the polypeptide comprising an amino acid sequence selected from the group consisting of SEQ ID NO: 1, SEQ ID NO:3, a fragment of SEQ ID NO: 1, and a fragment of SEQ ID NO:3, as well as an isolated and purified polynucleotide sequence which is complementary to the polynucleotide sequence encoding the polypeptide comprising the amino acid sequence selected from the group consisting of SEQ ID NO: 1, SEQ ID NO:3, a fragment of SEQ ID NO:1, and a fragment of SEQ ID NO:3.

The invention also provides an isolated and purified polynucleotide sequence comprising a polynucleotide sequence selected from the group consisting of SEQ ID NO:2, SEQ ID NO:4, a fragment of SEQ ID NO:2, and a fragment of SEQ ID NO:4. The invention further provides an isolated and purified polynucleotide variant having at least 90% polynucleotide identity to the polynucleotide sequence comprising a polynucleotide sequence selected from the group consisting of SEQ ID NO:2, SEQ ID NO:4, a fragment of SEQ ID NO:2, and a fragment of SEQ ID NO:4, as well as an isolated and purified polynucleotide sequence which is complementary to the polynucleotide sequence comprising a polynucleotide sequence selected from the group consisting of SEQ ID NO:2, SEQ ID NO:4, a fragment of SEQ ID NO:2, and a fragment of SEQ ID NO:4.

The invention further provides an expression vector containing at least a fragment of the polynucleotide sequence encoding the polypeptide comprising an amino acid sequence selected from the group consisting of SEQ ID NO: 1, SEQ ID NO:3, a fragment of SEQ ID NO: 1, and a fragment of SEQ ID NO:3. In another aspect, the expression vector is contained within a host cell.

The invention also provides a method for producing a polypeptide comprising the amino acid sequence of SEQ ID NO:1, SEQ ID NO:3, a fragment of SEQ D) NO:1, or a fragment of SEQ ID NO:3, the method comprising the steps of: (a) culturing the host cell containing an expression vector containing at least a fragment of a polynucleotide sequence encoding HUFA under conditions suitable for the expression of the polypeptide; and (b) recovering the polypeptide from the host cell culture.

The invention also provides a pharmaceutical composition comprising a substantially purified HUFA having the amino acid sequence of SEQ ID NO: 1, SEQ ID NO:3, a fragment of SEQ ID NO: 1, or a fragment of SEQ ID NO:3 in conjunction with a suitable pharmaceutical carrier.

The invention further includes a purified antibody which binds to a polypeptide comprising the amino acid sequence of SEQ ID NO: 1, SEQ ID NO:3, a fragment of SEQ ID NO: 1, or a fragment of SEQ ID NO:3, as well as a purified agonist and a purified antagonist to the polypeptide.

The invention also provides a method for treating or preventing a genetic disorder, the method comprising administering to a subject in need of such treatment an effective amount of a pharmaceutical composition comprising substantially purified HUFA.

The invention also provides a method for treating or preventing a neuronal disorder, the method comprising administering to a subject in need of such treatment an effective amount of a pharmaceutical composition comprising substantially purified HUFA-1.

The invention also provides a method for treating or preventing a cancer, the method comprising administering to a subject in need of such treatment an effective amount of a pharmaceutical composition comprising substantially purified HUFA- 1.

The invention also provides a method for treating or preventing an infectious disease, the method comprising administering to a subject in need of such treatment an effective amount of a pharmaceutical composition comprising substantially purified HUFA-2.

The invention also provides a method for treating or preventing a liver disorder, the method comprising administering to a subject in need of such treatment an effective amount of a pharmaceutical composition comprising substantially purified HUFA-2.

The invention also provides a method for treating or preventing a cardiac or skeletal muscle disorder, the method comprising administering to a subject in need of such treatment an effective amount of a pharmaceutical composition comprising substantially purified HUFA-2.

The invention also provides a method for detecting a polynucleotide encoding HUFA in a biological sample containing nucleic acids, the method comprising the steps of: (a) hybridizing the complement of the polynucleotide sequence encoding the polypeptide comprising SEQ ID NO: 1, SEQ ID NO:3, a fragment of SEQ ID NO: 1, or a fragment of SEQ ID NO:3 to at least one of the nucleic acids of the biological sample, thereby forming a hybridization complex; and (b) detecting the hybridization complex, wherein the presence of the hybridization complex correlates with the presence of a polynucleotide encoding HUFA in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, and 1D show the amino acid sequence (SEQ ID NO:1) and nucleic acid sequence (SEQ ID NO:2) of HUFA-1. The alignment was produced using MACDNASIS PRO™ software (Hitachi Software Engineering Co. Ltd., San Bruno, Calif.).

FIGS. 2A, 2B, 2C, 2D, 2E, 2F, 2G, and 2H show the amino acid sequence (SEQ ID NO:3) and nucleic acid sequence (SEQ ID NO:4) of HUFA-2. The alignment was produced using MACDNASIS PRO™ software.

FIGS. 3A, 3B, and 3C show the amino acid sequence alignments among HUFA-1 (Incyte Clone 1995961; SEQ ID NO: 1), *Saccharomyces cerevisiae* peroxisomal 2,4-dienoyl-CoA reductase (GI 730864; SEQ ID NO:5), human mitochondrial 2,4-dienoyl-CoA reductase (GI 602703; SEQ ID NO:6), and rat 2,4-dienoyl-CoA reductase (GI 111287; SEQ ID NO:7), produced using the multisequence alignment program of LASERGENE software (DNASTAR Inc., Madison, Wis.).

FIGS. 4A, 4B, and 4C show the amino acid sequence alignments among HUFA-2 (Incyte Clone 2595635; SEQ ID NO:3), human AU-binding protein/enoyl-CoA hydratase (GI 780241; SEQ ID NO:8), human enoyl-CoA hydratase (GI 1922287; SEQ ID NO:9), and human peroxisomal enoyl-CoA hydratase-like protein (GI 564065; SEQ ID NO: 10), produced using the multisequence alignment program of LASEGENE software.

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

DEFINITIONS

"HUFA," as used herein, refers to the amino acid sequences of substantially purified HUFA obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to HUFA, increases or prolongs the duration of the effect of HUFA. Agonists may include proteins, nucleic acids, carbohydrates, or any other molecules which bind to and modulate the effect of HUFA.

An "allele" or an "allelic sequence," as these terms are used herein, is an alternative form of the gene encoding HUFA. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HUFA, as described herein, include those sequences with deletions, insertions, or substitutions of different nucleotides, resulting in a polynucleotide the same HUFA or a polypeptide with at least one functional characteristic of HUFA. Included within this definition are polymorphisms which may or may not be readily detectable using a particular oligonucleotide probe of the polynucleotide encoding HUFA, and improper or unexpected hybridization to alleles, with a locus other than the normal chromosomal locus for the polynucleotide sequence encoding HUFA. The encoded protein may also be "altered," and may contain deletions, insertions, or substitutions of amino acid residues which produce a silent change and result in a functionally equivalent HUFA. Deliberate amino acid substitutions may be made on the basis of similarity in polarity, charge, solubility, hydrophobicity, hydrophilicity, and/or the amphipathic nature of the residues, as long as the biological or immunological activity of HUFA is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of HUFA which are preferably about 5 to about 15 amino acids in length and which retain some biological activity or immunological activity of HUFA. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual,* pp. 1–5, Cold Spring Harbor Press, Plainview, N.Y.)

The term "antagonist," as it is used herein, refers to a molecule which, when bound to HUFA, decreases the amount or the duration of the effect of the biological or immunological activity of HUFA. Antagonists may include proteins, nucleic acids, carbohydrates, antibodies, or any other molecules which decrease the effect of HUFA.

As used herein, the term "antibody" refers to intact molecules as well as to fragments thereof, such as Fab, F(ab')$_2$, and Fv fragments, which are capable of binding the epitopic determinant. Antibodies that bind HUFA polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific nucleic acid sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic HUFA, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding HUFA or fragments of HUFA may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

The phrase "consensus sequence," as used herein, refers to a nucleic acid sequence which has been resequenced to resolve uncalled bases, extended using XL-PCR (Perkin Elmer, Norwalk, Conn.) in the 5' and/or the 3' direction, and resequenced, or which has been assembled from the overlapping sequences of more than one Incyte Clone using a computer program for fragment assembly, such as the GEL-VIEW fragment assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding HUFA, by northern analysis is indicative of the presence of nucleic acids encoding HUFA in a sample, and thereby correlates with expression of the transcript from the polynucleotide encoding HUFA.

A "deletion," as the term is used herein, refers to a change in the amino acid or nucleotide sequence that results in the absence of one or more amino acid residues or nucleotides.

The term "derivative," as used herein, refers to the chemical modification of HUFA, of a polynucleotide sequence encoding HUFA, or of a polynucleotide sequence complementary to a polynucleotide sequence encoding HUFA. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains a at least one biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (LASERGENE software package, DNASTAR, Inc., Madison Wis.). The MEGALIGN program can create alignments between two or more sequences according to different methods, e.g., the Clustal Method. (Higgins, D. G. and P. M. Sharp (1988) Gene 73:237–244.) The Clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent identity between nucleic acid sequences can also be calculated by the Clustal Method, or by other methods known in the art, such as the Jotun Hein Method. (See, e.g., Hein, J. (1990) Methods in Enzymology 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex" as used herein, refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

The words "insertion" or "addition," as used herein, refer to changes in an amino acid or nucleotide sequence resulting in the addition of one or more amino acid residues or nucleotides, respectively, to the sequence found in the naturally occurring molecule.

The term "microarray," as used herein, refers to an array of distinct polynucleotides or oligonucleotides arrayed on a substrate, such as paper, nylon or any other type of membrane, filter, chip, glass slide, or any other suitable solid support.

The term "modulate," as it appears herein, refers to a change in the activity of HUFA. For example, modulation may cause an increase or a decrease in protein activity, binding characteristics, or any other biological, functional, or immunological properties of HUFA.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimers,""primers," "oligomers," and "probes," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (Nielsen, P. E. et al. (1993) Anticancer Drug Des. 8:53–63.)

The term "sample," as used herein, is used in its broadest sense. A biological sample suspected of containing nucleic acids encoding HUFA, or fragments thereof, or HUFA itself may comprise a bodily fluid; an extract from a cell, chromosome, organelle, or membrane isolated from a cell; a cell; genomic DNA, RNA, or cDNA (in solution or bound to a solid support); a tissue; a tissue print; and the like.

As used herein, the terms "specific binding" or "specifically binding" refer to that interaction between a protein or peptide and an agonist, an antibody, or an antagonist. The interaction is dependent upon the presence of a particular structure of the protein recognized by the binding molecule (i.e., the antigenic determinant or epitope). For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5× SSPE, 0.3% SDS, and 200 μg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, and refers to cells which transiently express the inserted DNA or RNA for limited periods of time.

A "variant" of HUFA, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software.

THE INVENTION

The invention is based on the discovery of new human fatty acid beta-oxidation enzymes (HUFA), the polynucleotides encoding HUFA, and the use of these compositions for the diagnosis, treatment, or prevention of genetic disorders, neuronal disorders, cancer, infectious diseases, liver disorders, and cardiac and skeletal muscle disorders.

Nucleic acids encoding the HUFA-1 of the present invention were first identified in Incyte Clone 1995961 from the human breast tumor cDNA library (BRSTTUT03) using a computer search for amino acid sequence alignments. A consensus sequence, SEQ ID NO:2, was derived from the following overlapping and/or extended nucleic acid sequences: Incyte Clones 270674 (HNT2NOT01), 1995961 (BRSTTUT03), and 2851728 (BRSTTUT13).

Figure 3A:
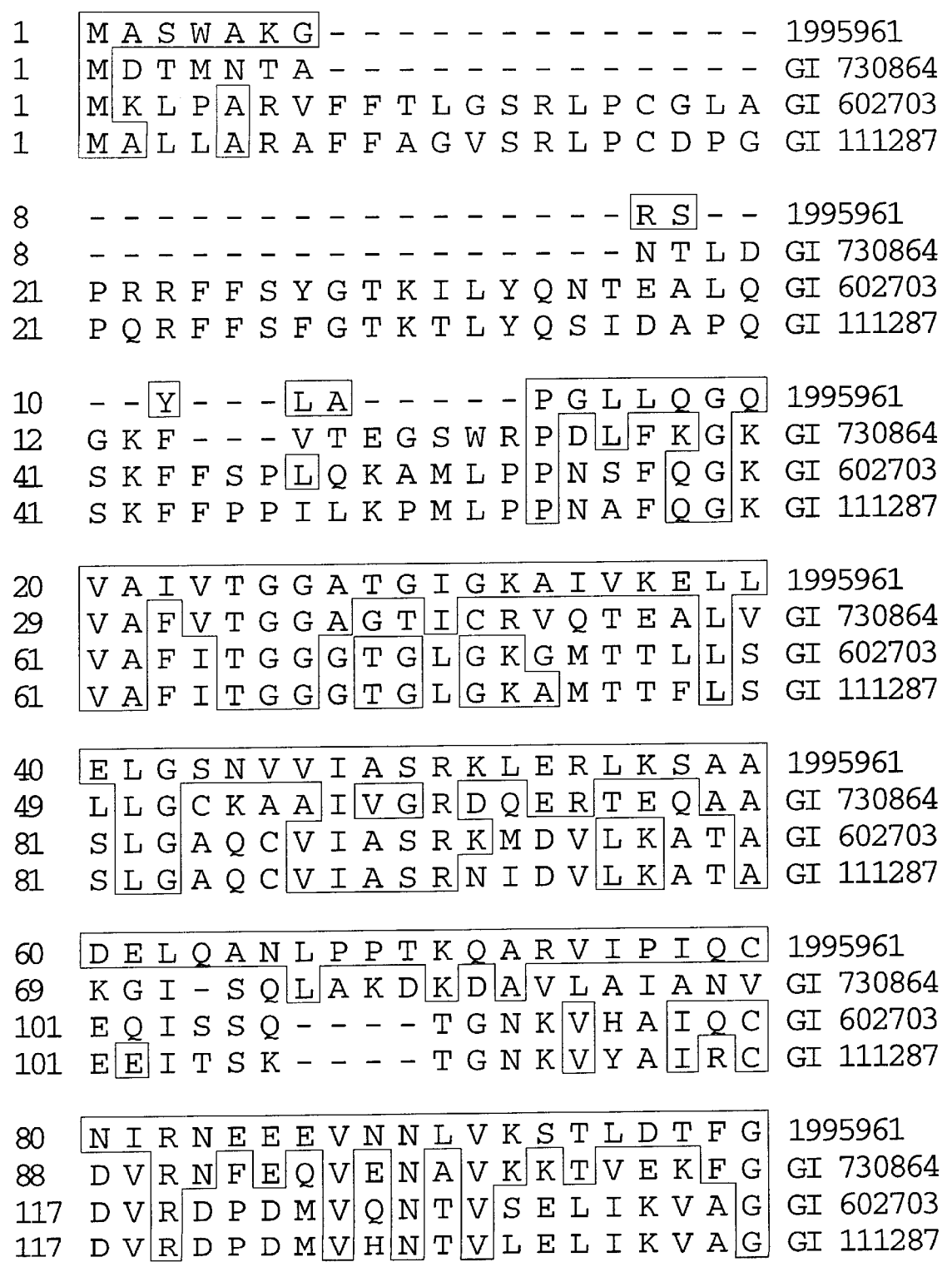
Figure 3B:
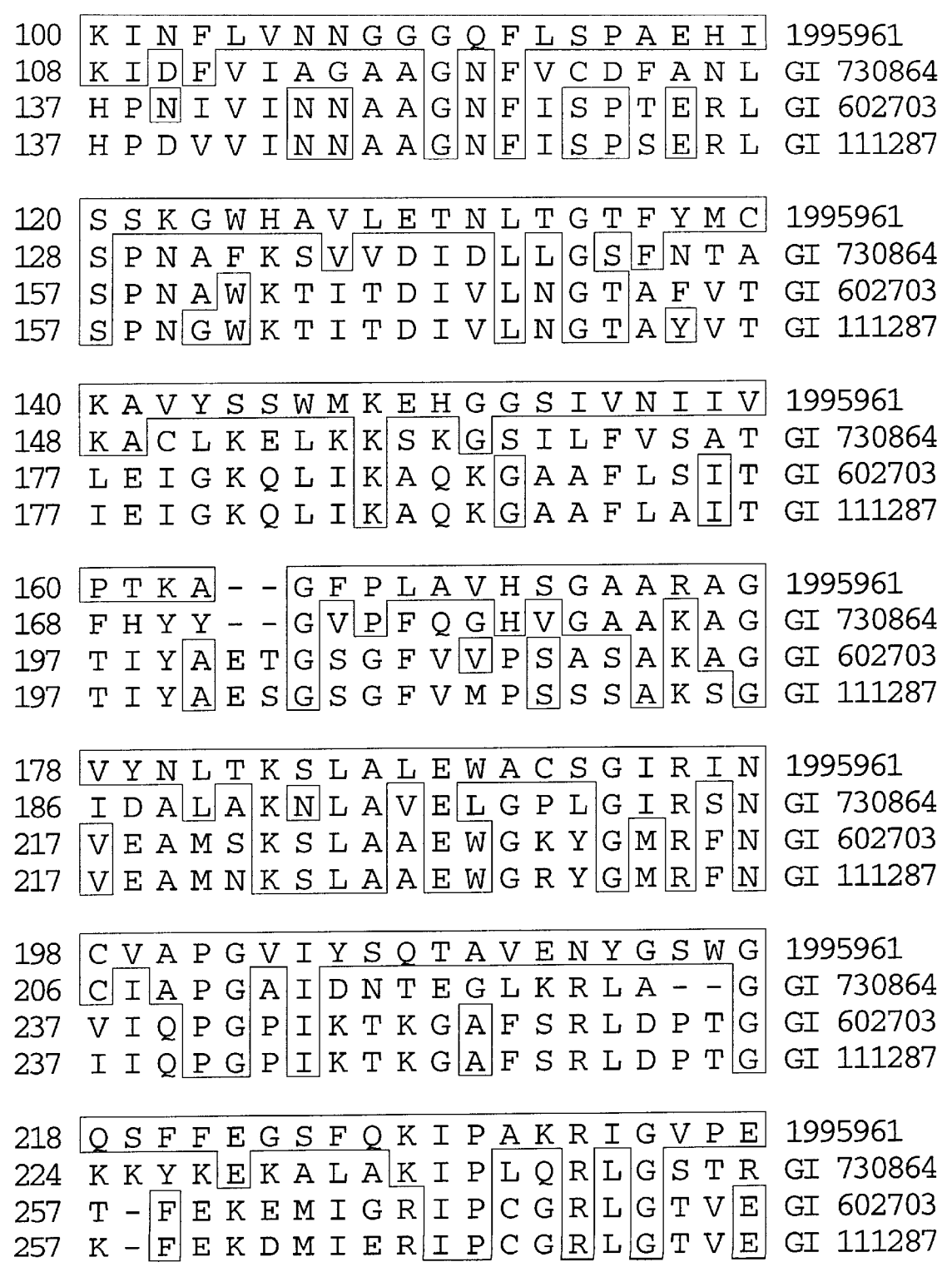
Figure 3C:
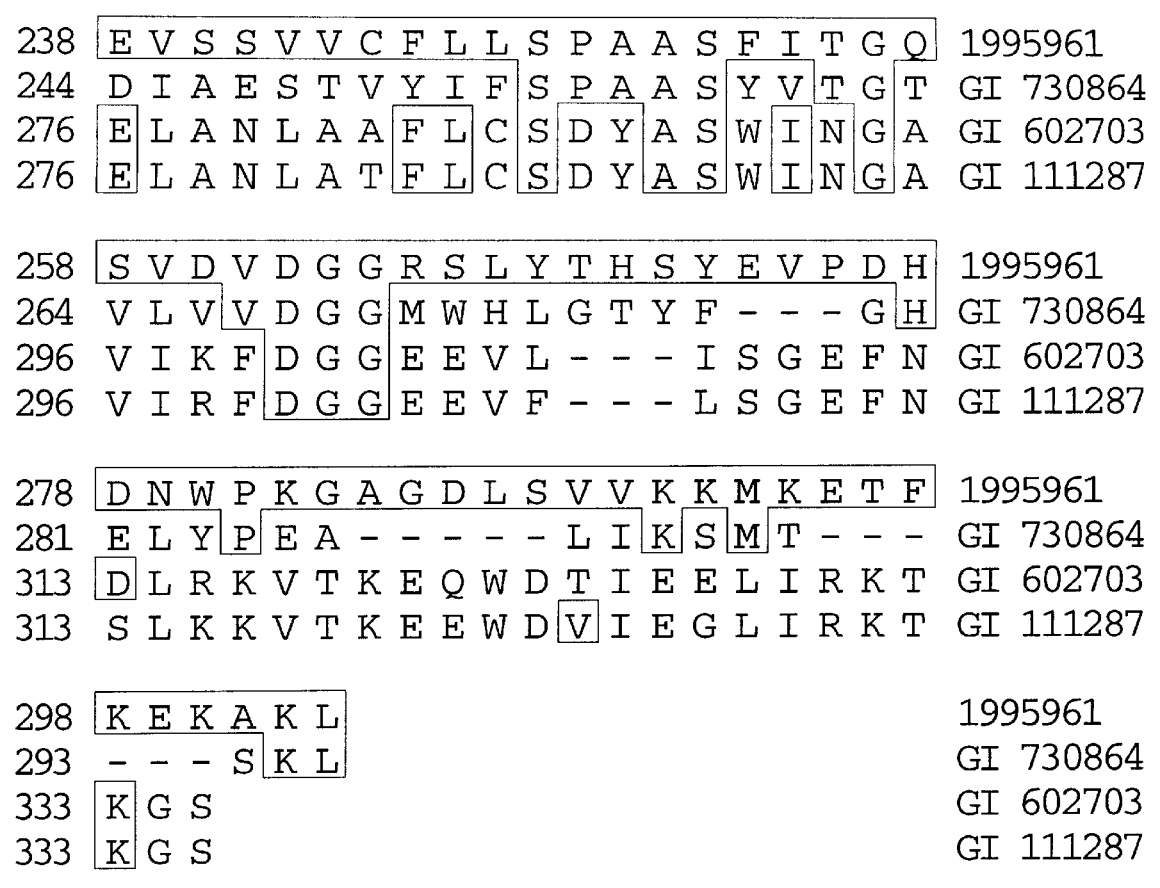

In one embodiment, the invention encompasses a polypeptide comprising the amino acid sequence of SEQ ID NO: 1 as shown in FIGS. 1A–1D. HUFA-1 is 303 amino acids in length and has a potential peroxisomal C-terminal targeting signal at A301KL. HUFA-1 has potential casein kinase II phosphorylation sites at residues S57, S93, S 114, T208, S219, and T296 and potential protein kinase C phosphorylation sites at residues S49, S 120, and T296. HUFA-1 has a potential NADPH-binding site motif at A21-E53, containing five of the eight consensus amino acid residues: A21, V23, G25, 134, and E53. As shown in FIGS. 3A–3C, HUFA-1 has chemical and structural homology with Saccharomyces cerevisiae peroxisomal 2,4-dienoyl-CoA reductase (GI 730864; SEQ ID NO:5), human mitochondrial 2,4-dienoyl-CoA reductase (GI 602703; SEQ ID NO:6), and rat 2,4-dienoyl-CoA reductase (GI 111287; SEQ ID NO:7). In particular, HUFA-1 and Saccharomyces cerevisiae peroxisomal 2,4-dienoyl-CoA reductase share 31% identity, HUFA-1 and human mitochondrial 2,4-dienoyl-CoA reductase share 31% identity, and HUFA-1 and rat 2,4-dienoyl-CoA reductase share 30% identity. In the region of the potential NADPH-binding site motif, A21-E53, HUFA-1 is 39% identical to Saccharomyces cerevisiae peroxisomal 2,4-dienoyl-CoA reductase, 52% identical to human mitochondrial 2,4-dienoyl-CoA reductase, and 52% identical to rat 2,4-dienoyl-CoA reductase. Northern analysis shows the expression of this sequence in various libraries, at least 81% of which are immortalized or cancerous and at least 9% of which involve immune response. Of particular note is the expression of HUFA-1 in libraries from breast and brain tissue.

Nucleic acids encoding the HUFA-2 of the present invention were first identified in Incyte Clone 2595635 from the human ovarian tumor cDNA library (OVARTUT02) using a computer search for amino acid sequence alignments. A consensus sequence, SEQ ID NO:4, was derived from the following overlapping and/or extended nucleic acid sequences: Incyte Clones 077607 (SYNORAB01), 416055 (BRSTNOT01), 782840 (MYOMNOT01), 1421780 (KIDNNOT09), 1449639 (PLACNOT02), 1474617 (LUNGTUT03), 1485974 (CORPNOT02), 1617081 (BRAITUT12), 1987379 (LUNGAST01), and 2595635 (OVARTUT02).

Figure 4A:
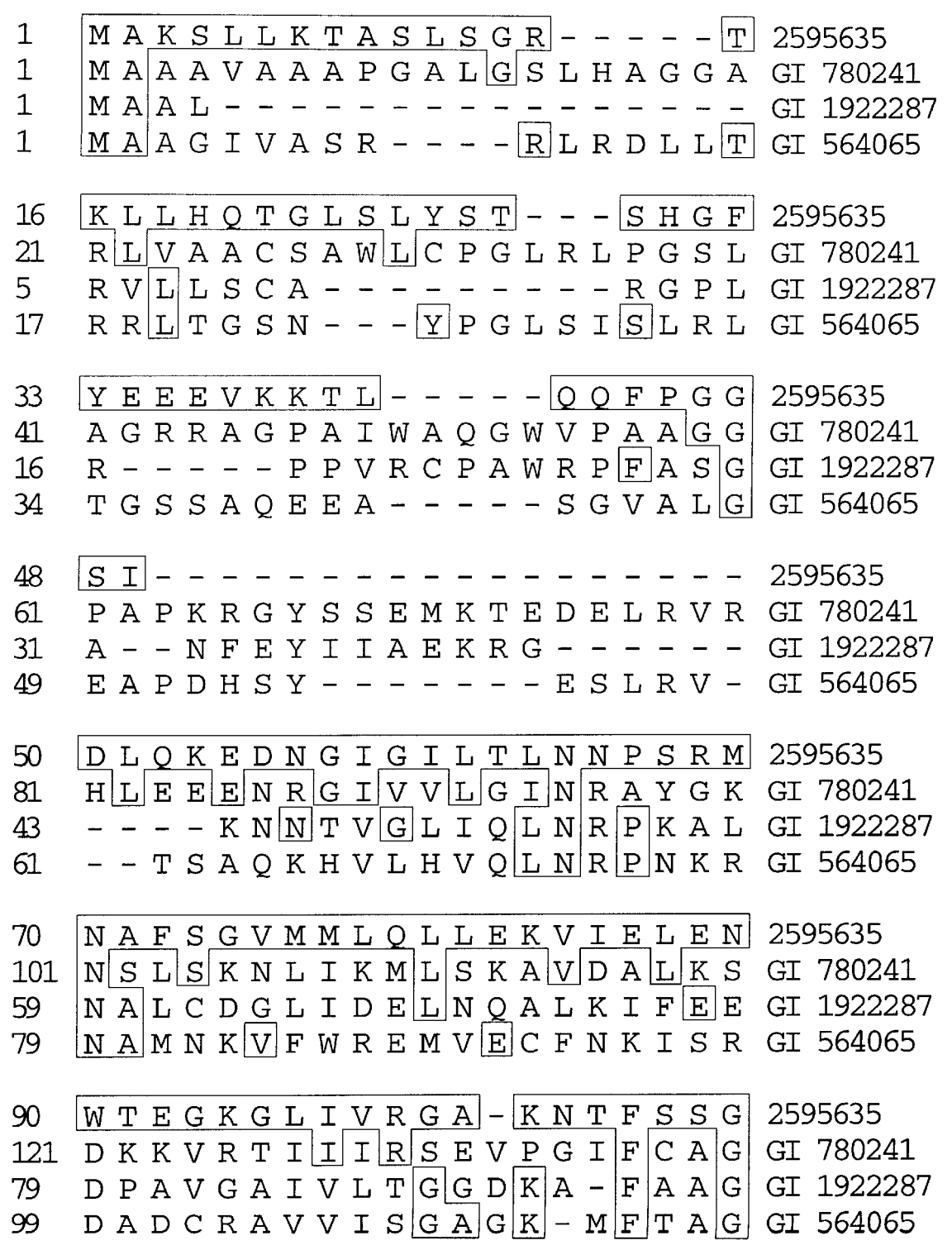
Figure 4B:
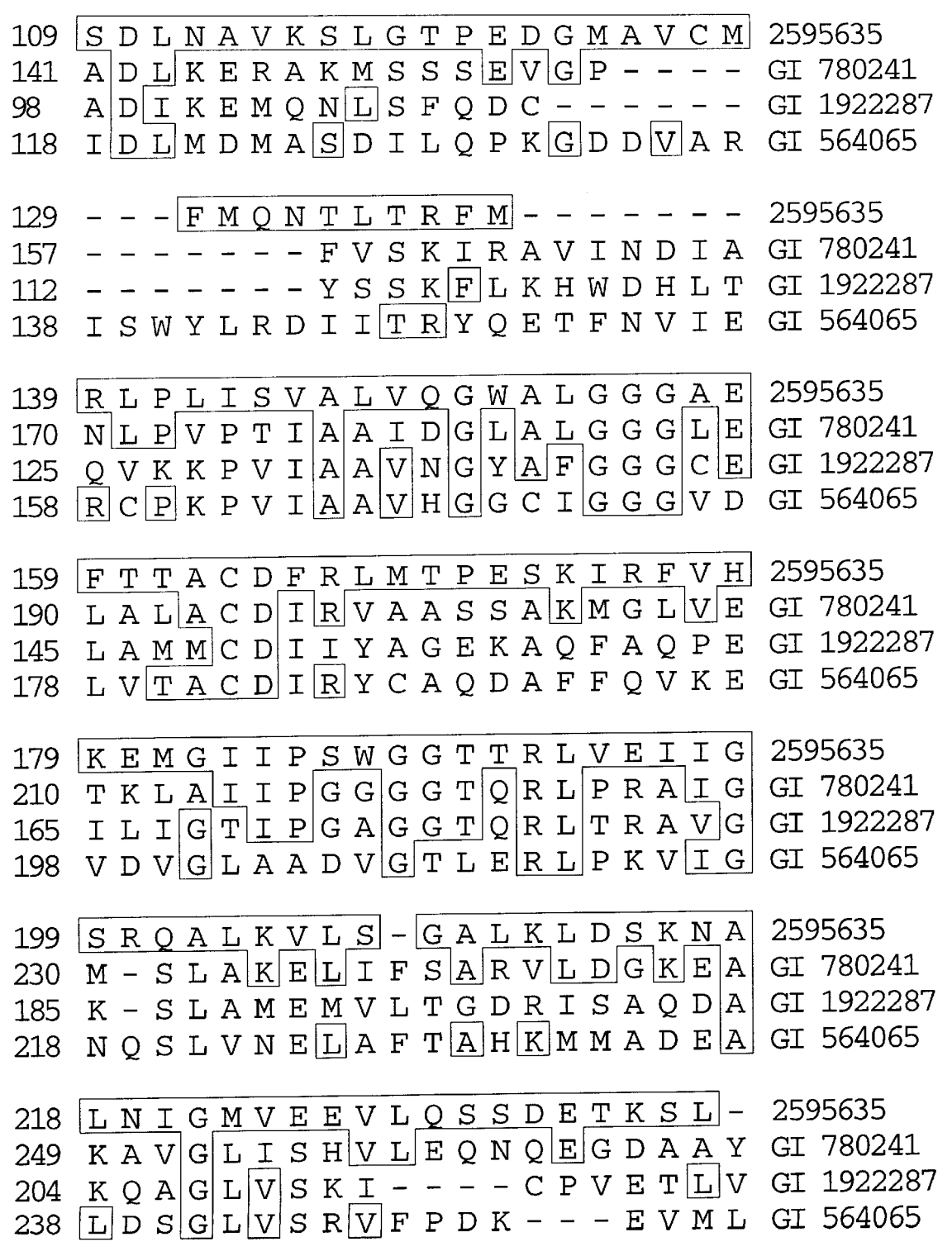
Figure 4C:
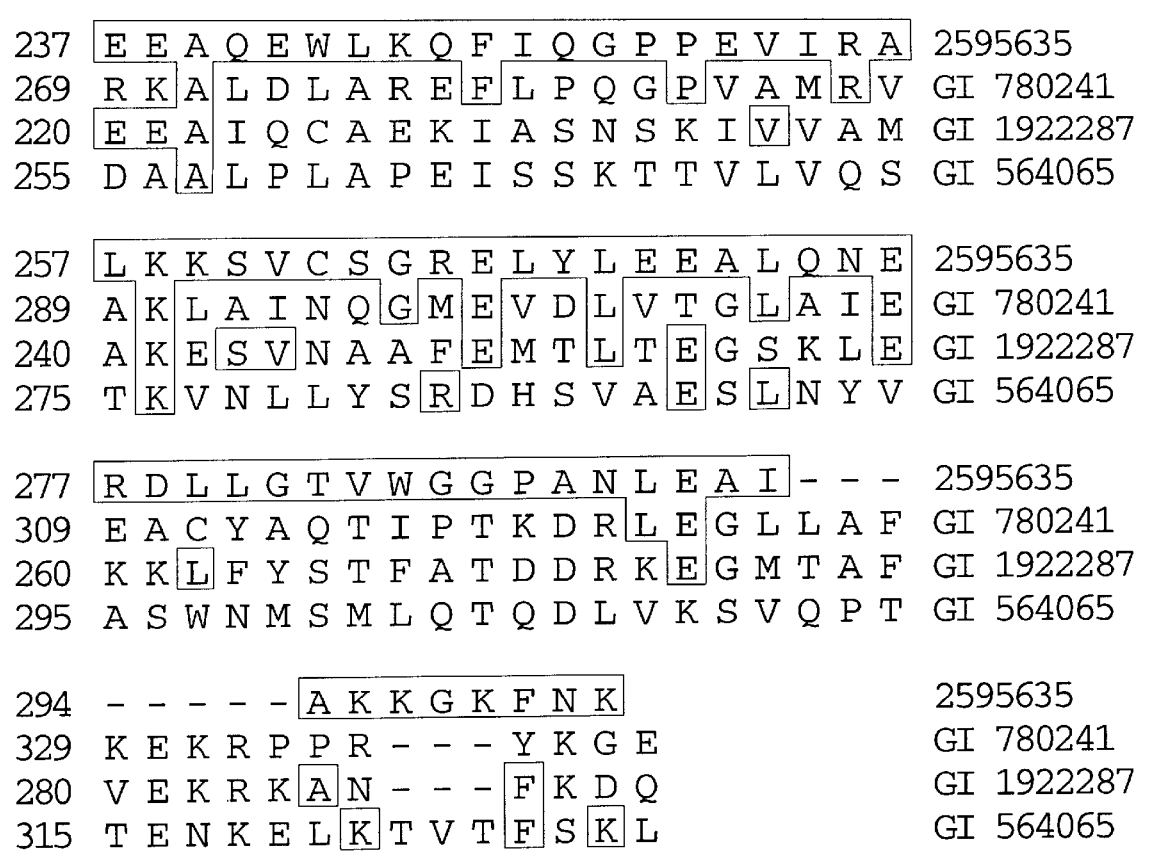

In one embodiment, the invention encompasses a polypeptide comprising the amino acid sequence of SEQ ID NO:3 as shown in FIGS. 2A–2H. HUFA-2 is 301 amino acids in length and has a potential mitochondrial N-terminal leader peptide from residues M1 through Y33. HUFA-2 has potential casein kinase II phosphorylation sites at residues S107, T119, T161, S229, S235, and S263, and potential protein kinase C phosphorylation sites at residues S12, T190, and S263. As shown in FIGS. 4A–4C, HUFA-2 has chemical and structural homology with human AU-binding protein/enoyl-CoA hydratase (GI 780241; SEQ ID NO:8), human enoyl-CoA hydratase (GI 1922287; SEQ ID NO:9), and human peroxisomal enoyl-CoA hydratase-like protein (GI 564065; SEQ ID NO: 10). In particular, HUFA-2 and human AU-binding protein/enoyl-CoA hydratase share 25% identity, HUFA-2 and human enoyl-CoA hydratase share 20% identity, and HUFA-2 and human peroxisomal enoyl-CoA hydratase-like protein share 21% identity. In particular, 10 of the 17 highly conserved residues around the enoyl-CoA hydratase active site are found in HUFA-2: G150, G154, G155, G156, E158, D164, G182, P185, G189, and G198. In particular, HUFA-2 contains the enoyl-CoA hydratase active site residue E158. Northern analysis shows the expression of this sequence in various libraries, at least 46% of which are immortalized or cancerous and at least 26% of which involve immune response. Of particular note is the expression of HUFA-2 in libraries prepared from heart and liver tissue.

The invention also encompasses HUFA variants. A preferred HUFA variant is one which has at least about 80%, more preferably at least about 90%, and most preferably at least about 95% amino acid sequence identity to the HUFA amino acid sequence, and which contains at least one functional or structural characteristic of HUFA.

The invention also encompasses polynucleotides which encode HUFA. In a particular embodiment, the invention encompasses a polynucleotide sequence comprising the sequence of SEQ ID NO:2, as shown in FIG. 1, which encodes a HUFA- 1. In a further embodiment, the invention encompasses the polynucleotide sequence comprising the sequence of SEQ ID NO:4, as shown in FIG. 2, which encodes a HUFA-2. The invention also encompasses a variant of a polynucleotide sequence encoding HUFA. In particular, such a variant polynucleotide sequence will have at least about 80%, more preferably at least about 90%, and most preferably at least about 95% polynucleotide sequence identity to the polynucleotide sequence encoding HUFA. A particular aspect of the invention encompasses a variant of SEQ ID NO:2 which has at least about 80%, more preferably at least about 90%, and most preferably at least about 95% polynucleotide sequence identity to SEQ ID NO:2. The invention further encompasses a polynucleotide variant of SEQ ID NO:4 having at least about 80%, more preferably at least about 90%, and most preferably at least about 95% polynucleotide sequence identity to SEQ ID NO:4. Any one of the polynucleotide variants described above can encode an amino acid sequence which contains at least one functional or structural characteristic of HUFA.

It will be appreciated by those skilled in the art that as a result of the degeneracy of the genetic code, a multitude of polynucleotide sequences encoding HUFA, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HUFA, and all such variations are to be considered as being specifically disclosed.

Although nucleotide sequences which encode HUFA and its variants are preferably capable of hybridizing to the nucleotide sequence of the naturally occurring HUFA under appropriately selected conditions of stringency, it may be advantageous to produce nucleotide sequences encoding HUFA or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HUFA and its derivatives without altering the encoded amino acid sequences include the production of RNA transcripts having more desirable properties, such as a greater half-life, than transcripts produced from the naturally occurring sequence.

The invention also encompasses production of DNA sequences which encode HUFA and HUFA derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HUFA or any fragment thereof.

Also encompassed by the invention are polynucleotide sequences that are capable of hybridizing to the claimed polynucleotide sequences, and, in particular, to those shown in SEQ ID NO:2, SEQ ID NO:4, a fragment of SEQ ID NO:2, or a fragment of SEQ ID NO:4 under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing are well known and generally available in the art and may be used to practice any of the embodiments of the invention. The methods may employ such enzymes as the Klenow fragment of DNA polymerase I, SEQUENASE (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system marketed by GIBCO/BRL (Gaithersburg, Md.). Preferably, the process is automated with machines such as the MICROLAB 2200 (Hamilton, Reno, Nev.), Peltier thermal cycler (PTC200; MJ Research, Watertown, Mass.) and the ABI CATALYST and 373 and 377 DNA SEQUENCERS (Perkin Elmer).

The nucleic acid sequences encoding HUFA may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus. (Sarkar, G. (1993) PCR Methods Applic. 2:318–322.) In particular, genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (Triglia, T. et al. (1988) Nucleic Acids Res. 16:8186.) The primers may be designed using commercially available software such as OLIGO 4.06 primer analysis software (National Biosciences Inc., Plymouth, Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (Lagerstrom, M. et al. (1991) PCR Methods Applic. 1:111–119.) In this method, multiple restriction enzyme digestions and ligations may be used to place an engineered double-stranded sequence into an unknown fragment of the DNA molecule before performing PCR. Another method which may be used to retrieve unknown sequences is that of Parker, J. D. et al. (1991; Nucleic Acids Res. 19:3055–3060). Additionally, one may use PCR, nested primers, and PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., GENETYPER and SEQUENCE NAVIGATOR, Perkin Elmer), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HUFA may be used in recombinant DNA molecules to direct expression of HUFA, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HUFA.

As will be understood by those of skill in the art, it may be advantageous to produce HUFA-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HUFA encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HUFA may be ligated to a heterologous sequence to encode a fusion protein. For example, to screen peptide libraries for inhibitors of HUFA activity, it may be useful to encode a chimeric HUFA protein that can be recognized by a commercially available antibody. A fusion protein may also be engineered to contain a cleavage site located between the HUFA encoding sequence and the heterologous protein sequence, so that HUFA may be cleaved and purified away from the heterologous moiety.

In another embodiment, sequences encoding HUFA may be synthesized, in whole or in part, using chemical methods well known in the art. (See, e.g., Caruthers, M. H. et al. (1980) Nucl. Acids Res. Symp. Ser. 215–223, and Horn, T. et al. (1980) Nucl. Acids Res. Symp. Ser. 225–232.) Alternatively, the protein itself may be produced using chemical methods to synthesize the amino acid sequence of HUFA, or a fragment thereof. For example, peptide synthesis can be performed using various solid-phase techniques (Roberge, J. Y. et al. (1995) Science 269:202–204) and automated synthesis may be achieved using the ABI 431A peptide synthesizer (Perkin Elmer).

The newly synthesized peptide may be substantially purified by preparative high performance liquid chromatography. (See, e.g., Chiez, R. M. and Regnier, F. Z. (1990) Methods Enzymol. 182:392–421.) The composition of the synthetic peptides may be confirmed by amino acid analysis or by sequencing. (See, e.g., the Edman degradation procedure described in Creighton, T. (1983) *Proteins, Structures and Molecular Principles,* WH Freeman and Co., New York, N.Y.). Additionally, the amino acid sequence of HUFA, or any part thereof, may be altered during direct synthesis and/or combined with sequences from other proteins, or any part thereof, to produce a variant polypeptide.

In order to express a biologically active HUFA, the nucleotide sequences encoding HUFA or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding HUFA and appropriate transcriptional and translational control elements. These methods include in vitro recombinant DNA techniques, synthetic techniques, and in vivo genetic recombination. Such techniques are described in Sambrook, J. et al. (1989; *Molecular Cloning, A Laboratory Manual,* ch. 4, 8, and 16–17, Cold Spring Harbor Press, Plainview, N.Y.) and Ausubel, F. M. et al. (1995 and periodic supplements; *Current Protocols in Molecular Biology*, ch. 9, 13, and 16, John Wiley & Sons, New York, N.Y.).

A variety of expression vector/host systems may be utilized to contain and express sequences encoding HUFA. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions of the vector (i.e., enhancers, promoters, and 5' and 3' untranslated regions) which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, La Jolla, Calif.) or PSPORT1 (GIBCO/BRL), and the like, may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HUFA, vectors based on SV40 or EBV may be used with an appropriate selectable marker.

In bacterial systems, a number of expression vectors may be selected depending upon the use intended for HUFA. For example, when large quantities of HUFA are needed for the induction of antibodies, vectors which direct high level expression of fusion proteins that are readily purified may be used. Such vectors include, but are not limited to, multifunctional *E. coli* cloning and expression vectors such as BLUESCRIPT (Stratagene), in which the sequence encoding HUFA may be ligated into the vector in frame with sequences for the amino-terminal Met and the subsequent 7 residues of β-galactosidase so that a hybrid protein is produced, pIN vectors (Van Heeke, G. and S. M. Schuster (1989) J. Biol. Chem. 264:5503–5509), and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters, such as alpha factor, alcohol oxidase, and PGH, may be used. For reviews, see Ausubel (supra) and Grant et al. (1987; Methods Enzymol. 153:516–544).

In cases where plant expression vectors are used, the expression of sequences encoding HUFA may be driven by any of a number of promoters. For example, viral promoters such as the 35S and 19S promoters of CaMV may be used alone or in combination with the omega leader sequence from TMV. (Takamatsu, N. (1987) EMBO J. 6:307–311.) Alternatively, plant promoters such as the small subunit of RUBISCO or heat shock promoters may be used. (Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. Such techniques are described in a number of generally available reviews. (See, for example, Hobbs, S. or Murry, L. E. in *McGraw Hill Yearbook of Science and Technology* (1992) McGraw Hill, New York, N.Y.; pp. 191–196.)

An insect system may also be used to express HUFA. For example, in one such system, *Autographa californica* nuclear polyhedrosis virus (AcNPV) is used as a vector to express foreign genes in *Spodoptera frugiperda* cells or in Trichoplusia larvae. The sequences encoding HUFA may be cloned into a non-essential region of the virus, such as the polyhedrin gene, and placed under control of the polyhedrin promoter. Successful insertion of HUFA will render the polyhedrin gene inactive and produce recombinant virus lacking coat protein. The recombinant viruses may then be used to infect, for example, *S. frugiperda* cells or Trichoplusia larvae in which HUFA may be expressed. (Engelhard, E. K. et al. (1994) Proc. Nat. Acad. Sci. 91:3224–3227.)

In mammalian host cells, a number of viral-based expression systems may be utilized. In cases where an adenovirus is used as an expression vector, sequences encoding HUFA may be ligated into an adenovirus transcription/translation complex consisting of the late promoter and tripartite leader sequence. Insertion in a non-essential E1 or E3 region of the viral genome may be used to obtain a viable virus which is capable of expressing HUFA in infected host cells. (Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 kb to 10 Mb are constructed and delivered via conventional delivery methods (liposomes, polycationic amino polymers, or vesicles) for therapeutic purposes.

Specific initiation signals may also be used to achieve more efficient translation of sequences encoding HUFA. Such signals include the ATG initiation codon and adjacent sequences. In cases where sequences encoding HUFA and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used, such as those described in the literature. (Scharf, D. et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and WI38), are available from the American Type Culture Collection (ATCC, Manassas, Va.) and may be chosen to ensure the correct modification and processing of the foreign protein.

For long term, high yield production of recombinant proteins, stable expression is preferred. For example, cell lines capable of stably expressing HUFA can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes (Wigler, M. et al. (1977) Cell 11:223–32) and adenine phosphoribosyl-transferase genes (Lowy, I. et al. (1980) Cell 22:817–23), which can be employed in tk$^-$ or apf$^-$ cells, respectively. Also, antimetabolite, antibiotic, or herbicide resistance can be used as the basis for selection. For example, dhfr confers resistance to methotrexate (Wigler, M. et al. (1980) Proc. Natl. Acad. Sci. 77:3567–70); npt confers resistance to the aminoglycosides neomycin and G-418 (Colbere-Garapin, F. et al (1981) J. Mol. Biol. 150:1–14); and als or pat confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine. (Hartman, S. C. and R. C. Mulligan (1988) Proc. Natl. Acad. Sci. 85:8047–51.) Recently, the use of visible markers has gained popularity with such markers as anthocyanins, β glucuronidase and its substrate GUS, and luciferase and its substrate luciferin. These markers can be used not only to identify transformants, but also to quantify the amount of transient or stable protein expression attributable to a specific vector system. (Rhodes, C.A. et al. (1995) Methods Mol. Biol. 55:121–131.)

Although the presence/absence of marker gene expression suggests that the gene of interest is also present, the presence and expression of the gene may need to be confirmed. For example, if the sequence encoding HUFA is inserted within a marker gene sequence, transformed cells containing sequences encoding HUFA can be identified by the absence of marker gene function. Alternatively, a marker gene can be placed in tandem with a sequence encoding HUFA under the control of a single promoter. Expression of the marker gene in response to induction or selection usually indicates expression of the tandem gene as well.

Alternatively, host cells which contain the nucleic acid sequence encoding HUFA and express HUFA may be identified by a variety of procedures known to those of skill in the art. These procedures include, but are not limited to, DNA-DNA or DNA-RNA hybridizations and protein bio-assay or immunoassay techniques which include membrane, solution, or chip based technologies for the detection and/or quantification of nucleic acid or protein sequences.

The presence of polynucleotide sequences encoding HUFA can be detected by DNA-DNA or DNA-RNA hybridization or amplification using probes or fragments or fragments of polynucleotides encoding HUFA. Nucleic acid amplification based assays involve the use of oligonucleotides or oligomers based on the sequences encoding HUFA to detect transformants containing DNA or RNA encoding HUFA.

A variety of protocols for detecting and measuring the expression of HUFA, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HUFA is preferred, but a competitive binding assay may be employed. These and other assays are well described in the art, for example, in Hampton, R. et al. (1990; *Serological Methods, a Laboratory Manual*, Section IV, APS Press, St Paul, Minn.) and in Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HUFA include oligolabeling, nick translation, end-labeling, or PCR amplification using a labeled nucleotide. Alternatively, the sequences encoding HUFA, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Mich.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HUFA may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HUFA may be designed to contain signal sequences which direct secretion of HUFA through a prokaryotic or eukaryotic cell membrane. Other constructions may be used to join sequences encoding HUFA to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences, such as those specific for Factor XA or enterokinase (Invitrogen, San Diego, Calif.), between the purification domain and the HUFA encoding sequence may be used to facilitate purification. One such expression vector provides for expression of a fusion protein containing HUFA and a nucleic acid encoding 6 histidine residues preceding a thioredoxin or an enterokinase cleavage site. The histidine residues facilitate purification on immobilized metal ion affinity chromatography (IMIAC; described in Porath, J. et al. (1992) Prot. Exp. Purif. 3: 263–281)), while the enterokinase cleavage site provides a means for purifying HUFA from the fusion protein. A discussion of vectors which contain fusion proteins is provided in Kroll, D. J. et al. (1993; DNA Cell Biol. 12:441–453).

Fragments of HUFA may be produced not only by recombinant production, but also by direct peptide synthesis using solid-phase techniques. (Merrifield J. (1963) J. Am. Chem. Soc. 85:2149–2154.) Protein synthesis may be performed by manual techniques or by automation. Automated synthesis may be achieved, for example, using the Applied Biosystems 431A peptide synthesizer (Perkin Elmer). Various fragments of HUFA may be synthesized separately and then combined to produce the full length molecule.

THERAPEUTICS

Chemical and structural homology exists among HUFA-1 and peroxisomal 2,4-dienoyl-CoA reductase from *Saccharomyces cerevisiae* (GI 730864), mitochondrial 2,4-dienoyl-CoA reductase from human (GI 602703), and 2,4-dienoyl-CoA reductase from rat (GI 111287). In addition, HUFA-1 is expressed in cancerous and brain tissue. Therefore, HUFA-1 appears to play a role in genetic disorders, neuronal disorders, and cancer.

Chemical and structural homology exists among HUFA-2 and AU-binding protein/enoyl-CoA hydratase from human (GI 780241), enoyl-CoA hydratase from human (GI 1922287), and peroxisomal enoyl-CoA hydratase-like protein from human (GI 564065). In addition, HUFA-2 is expressed in heart and liver tissue. Therefore, HUFA-2 appears to play a role in genetic disorders, infectious diseases, liver disorders, and cardiac and skeletal muscle disorders.

Therefore, in one embodiment, HUFA or a fragment or derivative thereof may be administered to a subject to treat or prevent a genetic disorder. Such disorders can include, but are not limited to, adrenoleukodystrophy, Alport's syndrome, choroideremia, Duchenne and Becker muscular dystrophy, Down's syndrome, cystic fibrosis, chronic granulomatous disease, Gaucher's disease, Huntington's chorea, Marfan's syndrome, muscular dystrophy, myotonic dystrophy, pycnodysostosis, Refsum's syndrome, retinoblastoma, sickle cell anemia, thalassemia, Werner syndrome, von Willebrand's disease, Wilm's tumor, Zellweger syndrome, peroxisomal acyl-CoA oxidase deficiency, peroxisomal thiolase deficiency, peroxisomal bifunctional protein deficiency, mitochondrial carnitine palmitoyl transferase and carnitine deficiency, mtiochondrial very-long-chain acyl-CoA dehydrogenase deficiency, mitochondrial medium-chain acyl-CoA dehydrogenase deficiency, mitochondrial short-chain acyl-CoA dehydrogenase deficiency, mitochondrial electron transport flavoprotein and electron transport flavoprotein:ubiquinone oxidoreductase deficiency, mitochondrial trifunctional protein deficiency, and mitochondrial short-chain 3-hydroxyacyl-CoA dehydrogenase deficiency.

In another embodiment, a vector capable of expressing HUFA or a fragment or derivative thereof may be administered to a subject to treat or prevent a genetic disorder including, but not limited to, those described above.

In a further embodiment, a pharmaceutical composition comprising a substantially purified HUFA in conjunction with a suitable pharmaceutical carrier may be administered to a subject to treat or prevent a genetic disorder including, but not limited to, those provided above.

In still another embodiment, an agonist which modulates the activity of HUFA may be administered to a subject to treat or prevent a genetic disorder including, but not limited to, those listed above.

In another embodiment, HUFA-1 or a fragment or derivative thereof may be administered to a subject to treat or prevent a neuronal disorder. Such disorders can include, but are not limited to, akathesia, Alzheimer's disease, amnesia, amyotrophic lateral sclerosis, bipolar disorder, catatonia, cerebral neoplasms, dementia, depression, diabetic neuropathy, Down's syndrome, tardive dyskinesia, dystonias, epilepsy, Huntington's disease, multiple sclerosis, neurofibromatosis, Parkinson's disease, paranoid psychoses, postherpetic neuralgia, schizophrenia, and Tourette's disorder.

In another embodiment, a vector capable of expressing HUFA-1 or a fragment or derivative thereof may be administered to a subject to treat or prevent a neuronal disorder including, but not limited to, those described above.

In a further embodiment, a pharmaceutical composition comprising a substantially purified HUFA-1 in conjunction with a suitable pharmaceutical carrier may be administered to a subject to treat or prevent a neuronal disorder including, but not limited to, those provided above.

In still another embodiment, an agonist which modulates the activity of HUFA-1 may be administered to a subject to treat or prevent a neuronal disorder including, but not limited to, those listed above.

In another embodiment, HUFA-1 or a fragment or derivative thereof may be administered to a subject to treat or prevent a cancer. Cancers can include, but are not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

In another embodiment, a vector capable of expressing HUFA-1 or a fragment or derivative thereof may be administered to a subject to treat or prevent a cancer including, but not limited to, those described above.

In a further embodiment, a pharmaceutical composition comprising a substantially purified HUFA-1 in conjunction with a suitable pharmaceutical carrier may be administered to a subject to treat or prevent a cancer including, but not limited to, those provided above.

In still another embodiment, an agonist which modulates the activity of HUFA may be administered to a subject to treat or prevent a cancer including, but not limited to, those listed above.

In another embodiment, HUFA-2 or a fragment or derivative thereof may be administered to a subject to treat or prevent an infectious disease. Such diseases can include, but are not limited to, viral infections: adenoviruses (ARD, pneumonia), arenaviruses (lymphocytic choriomeningitis), bunyaviruses (Hantavirus), coronaviruses (pneumonia, chronic bronchitis), hepadnaviruses (hepatitis), herpesviruses (HSV, VZV, Epstein-Barr virus, cytomegalovirus), flaviviruses (yellow fever), orthomyxoviruses (influenza), papillomaviruses (cancer), paramyxoviruses (measles, mumps), picornoviruses (rhinovirus, poliovirus, coxsackievirus), polyomaviruses (BK virus, JC virus), poxviruses (smallpox), reovirus (Colorado tick fever), retroviruses (HIV, HTLV), rhabdoviruses (rabies), rotaviruses (gastroenteritis), and togaviruses (encephalitis, rubella); bacterial infections, fungal infections, parasitic infections, protozoal infections, and helminthic infections.

In another embodiment, a vector capable of expressing HUFA-2 or a fragment or derivative thereof may be administered to a subject to treat or prevent an infectious disease including, but not limited to, those described above.

In a further embodiment, a pharmaceutical composition comprising a substantially purified HUFA-2 in conjunction with a suitable pharmaceutical carrier may be administered to a subject to treat or prevent an infectious disease including, but not limited to, those provided above.

In still another embodiment, an agonist which modulates the activity of HUFA-2 may be administered to a subject to treat or prevent an infectious disease including, but not limited to, those listed above.

In another embodiment, HUFA-2 or a fragment or derivative thereof may be administered to a subject to treat or prevent a liver disorder. Such disorders can include, but are not limited to, cirrhosis, jaundice, cholestasis, hereditary hyperbilirubinemia, hepatic encephalopathy, hepatorenal syndrome, hepatitis, hepatic steatosis, hemochromatosis, Wilson's disease, alpha,-antitrypsin deficiency, Reye's syndrome, primary sclerosing cholangitis, liver infarction, portal vein obstruction and thrombosis, passive congestion, centrilobular necrosis, peliosis hepatis, hepatic vein thrombosis, veno-occlusive disease, preeclampsia, eclampsia, acute fatty liver of pregnancy, intrahepatic cholestasis of pregnancy, and hepatic tumors including nodular hyperplasias, adenomas, and carcinomas.

In another embodiment, a vector capable of expressing HUFA-2 or a fragment or derivative thereof may be administered to a subject to treat or prevent a liver disorder including, but not limited to, those described above.

In a further embodiment, a pharmaceutical composition comprising a substantially purified HUFA-2 in conjunction with a suitable pharmaceutical carrier may be administered to a subject to treat or prevent a liver disorder including, but not limited to, those provided above.

In still another embodiment, an agonist which modulates the activity of HUFA-2 may be administered to a subject to treat or prevent a liver disorder including, but not limited to, those listed above.

In another embodiment, HUFA-2 or a fragment or derivative thereof may be administered to a subject to treat or prevent a cardiac or skeletal muscle disorder. Such disorders can include, but are not limited to, cardiomyopathy, myocarditis, Duchenne's muscular dystrophy, Becker's muscular dystrophy, myotonic dystrophy, central core disease, nemaline myopathy, centronuclear myopathy, lipid myopathy, mitochondrial myopathy, infectious myositis, polymyositis, dermatomyositis, inclusion body myositis, thyrotoxic myopathy, and ethanol myopathy.

In another embodiment, a vector capable of expressing HUFA-2 or a fragment or derivative thereof may be administered to a subject to treat or prevent a cardiac or skeletal muscle disorder including, but not limited to, those described above.

In a further embodiment, a pharmaceutical composition comprising a substantially purified HUFA-2 in conjunction with a suitable pharmaceutical carrier may be administered to a subject to treat or prevent a cardiac or skeletal muscle disorder including, but not limited to, those provided above.

In still another embodiment, an agonist which modulates the activity of HUFA-2 may be administered to a subject to treat or prevent a cardiac or skeletal muscle disorder including, but not limited to, those listed above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HUFA may be produced using methods which are generally known in the art. In particular, purified HUFA may be used to produce antibodies or to screen libraries of pharmaceutical agents to identify those which specifically bind HUFA. Antibodies to HUFA may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HUFA or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HUFA have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HUFA amino acids may be fused with those of another protein, such as KLH, and antibodies to the chimeric molecule may be produced.

Monoclonal antibodies to HUFA may be prepared using any technique which provides for the production of antibody molecules by continuous cell lines in culture. These include, but are not limited to, the hybridoma technique, the human B-cell hybridoma technique, and the EBV-hybridoma technique. (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce HUFA-specific single chain antibodies. Antibodies with related specificity, but of distinct idiotypic composition, may be generated by chain shuffling from random combinatorial immunoglobulin libraries. (Burton D. R. (1991) Proc. Natl. Acad. Sci. 88:11120–11123.)

Antibodies may also be produced by inducing in vivo production in the lymphocyte population or by screening immunoglobulin libraries or panels of highly specific binding reagents as disclosed in the literature. (Orlandi, R. et al. (1989) Proc. Natl. Acad. Sci. 86: 3833–3837, and Winter, G. et al. (1991) Nature 349:293–299.)

Antibody fragments which contain specific binding sites for HUFA may also be generated. For example, such fragments include, but are not limited to, F(ab)2 fragments produced by pepsin digestion of the antibody molecule and Fab fragments generated by reducing the disulfide bridges of the F(ab)2 fragments. Alternatively, Fab expression libraries may be constructed to allow rapid and easy identification of monoclonal Fab fragments with the desired specificity. (Huse, W. D. et al. (1989) Science 254:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HUFA and its specific antibody. A two-site, monoclonal-based immunoassay utilizing monoclonal antibodies reactive to two non-interfering HUFA epitopes is preferred, but a competitive binding assay may also be employed. (Maddox, supra.)

In another embodiment of the invention, the polynucleotides encoding HUFA, or any fragment or complement thereof, may be used for therapeutic purposes. In one aspect, the complement of the polynucleotide encoding HUFA may be used in situations in which it would be desirable to block the transcription of the MRNA. In particular, cells may be transformed with sequences complementary to polynucleotides encoding HUFA. Thus, complementary molecules or fragments may be used to modulate HUFA activity, or to achieve regulation of gene function. Such technology is now well known in the art, and sense or antisense oligonucleotides or larger fragments can be designed from various locations along the coding or control regions of sequences encoding HUFA.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequence complementary to the polynucleotides of the gene encoding HUFA. These techniques are described, for example, in Sambrook (supra) and in Ausubel (supra).

Genes encoding HUFA can be turned off by transforming a cell or tissue with expression vectors which express high levels of a polynucleotide or fragment thereof encoding HUFA. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HUFA. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (Gee, J. E. et al. (1994) in Huber, B. E. and B. I. Carr, *Molecular and Immunologic Approaches*, pp. 163–177, Futura Publishing Co., Mt. Kisco, N.Y.) A complementary sequence or antisense molecule may also be designed to block translation of MRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules specifically and efficiently catalyze endonucleolytic cleavage of sequences encoding HUFA.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HUFA. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art, such as those described in Goldman, C. K. et al. (1997; Nature Biotechnology 15:462–466).

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HUFA, antibodies to HUFA, and mimetics, agonists, antagonists, or inhibitors of HUFA. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HUFA, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays of neoplastic cells, for example, or in animal models, usually mice, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HUFA or fragments thereof, antibodies of HUFA, and agonists, antagonists or inhibitors of HUFA, which ameliorates the symptoms or condition. Therapeutic efficacy and toxicity may be determined by standard pharmaceutical procedures in cell cultures or with experimental animals, such as by calculating the ED50 (the dose therapeutically effective in 50% of the population) or LD50 (the dose lethal to 50% of the population) statistics. The dose ratio of toxic to therapeutic effects is the therapeutic index, which can be expressed as the LD50/ED50 ratio. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on the half-life and clearance rate of the particular formulation.

Normal dosage amounts may vary from 0.1 μg to 100,000 μg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which specifically bind HUFA may be used for the diagnosis of disorders characterized by expression of HUFA, or in assays to monitor patients being treated with HUFA or agonists, antagonists, and inhibitors of HUFA. Antibodies useful for diagnostic purposes may be prepared in the same manner as those described above for therapeutics. Diagnostic assays for HUFA include methods which utilize the antibody and a label to detect HUFA in human body fluids or in extracts of cells or tissues. The antibodies may be used with or without modification, and may be labeled by covalent or non-covalent joining with a reporter molecule. A wide variety of reporter molecules, several of which are described above, are known in the art and may be used.

A variety of protocols for measuring HUFA, including ELISAs, RIAs, and FACS, are known in the art and provide a basis for diagnosing altered or abnormal levels of HUFA expression. Normal or standard values for HUFA expression are established by combining body fluids or cell extracts taken from normal mammalian subjects, preferably human, with antibody to HUFA under conditions suitable for complex formation. The amount of standard complex formation may be quantified by various methods, preferably by photometric means. Quantities of HUFA expressed in subject, samples from biopsied tissues are compared with the standard values. Deviation between standard and subject values establishes the parameters for diagnosing disease.

In another embodiment of the invention, the polynucleotides encoding HUFA may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HUFA may be correlated with disease. The diagnostic assay may be used to distinguish between absence, presence, and excess expression of HUFA, and to monitor regulation of HUFA levels during therapeutic intervention.

In one aspect, hybridization with PCR probes which are capable of detecting polynucleotide sequences, including genomic sequences, encoding HUFA or closely related molecules may be used to identify nucleic acid sequences which encode HUFA. The specificity of the probe, whether it is made from a highly specific region (e.g., the 5' regulatory region) or from a less specific region (e.g., the 3' coding region), and the stringency of the hybridization or amplification (maximal, high, intermediate, or low), will determine whether the probe identifies only naturally occurring sequences encoding HUFA, alleles, or related sequences.

Probes may also be used for the detection of related sequences, and should preferably contain at least 50% of the nucleotides from any of the HUFA encoding sequences. The hybridization probes of the subject invention may be DNA or RNA and may be derived from the sequences of SEQ ID NO:2 and SEQ ID NO:4 or from genomic sequences including promoter and enhancer elements and introns of the naturally occurring HUFA.

Means for producing specific hybridization probes for DNAs encoding HUFA include the cloning of polynucleotide sequences encoding HUFA or HUFA derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotide sequences encoding HUFA may be used for the diagnosis of a disorder associated with expression of HUFA. Examples of such disorders include, but are not limited to, genetic disorders, such as adrenoleukodystrophy, Alport's syndrome, choroideremia, Duchenne and Becker muscular dystrophy, Down's syndrome, cystic fibrosis, chronic granulomatous disease, Gaucher's disease, Huntington's chorea, Marfan's syndrome, muscular dystrophy, myotonic dystrophy, pycnodysostosis, Refsum's syndrome, retinoblastoma, sickle cell anemia, thalassemia, Werner syndrome, von Willebrand's disease, Wilm's tumor, Zellweger syndrome, peroxisomal acyl-CoA oxidase deficiency, peroxisomal thiolase deficiency, peroxisomal bifunctional protein deficiency, mitochondrial carnitine palmitoyl transferase and carnitine deficiency, mtiochondrial very-long-chain acyl-CoA dehydrogenase deficiency, mitochondrial medium-chain acyl-CoA dehydrogenase deficiency, mitochondrial short-chain acyl-CoA dehydrogenase deficiency, mitochondrial electron transport flavoprotein and electron transport flavoprotein:ubiquinone oxidoreductase deficiency, mitochondrial trifunctional protein deficiency, and mitochondrial short-chain 3-hydroxyacyl-CoA dehydrogenase deficiency.

Polynucleotide sequences encoding HUFA-1 may be used for the diagnosis of a disorder associated with expression of HUFA-1. Examples of such disorders include, but are not limited to, neuronal disorders, such as akathesia, Alzheimer's disease, amnesia, amyotrophic lateral sclerosis, bipolar disorder, catatonia, cerebral neoplasms, dementia, depression, diabetic neuropathy, Down's syndrome, tardive dyskinesia, dystonias, epilepsy, Huntington's disease, multiple sclerosis, neurofibromatosis, Parkinson's disease, paranoid psychoses, postherpetic neuralgia, schizophrenia, and Tourette's disorder; and cancers, including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus.

Polynucleotide sequences encoding HUFA-2 may be used for the diagnosis of a disorder associated with expression of HUFA-2. Examples of such disorders include, but are not limited to, infectious diseases, including viral infections: adenoviruses (ARD, pneumonia), arenaviruses (lymphocytic choriomeningitis), bunyaviruses (Hantavirus), coronaviruses (pneumonia, chronic bronchitis), hepadnaviruses (hepatitis), herpesviruses (HSV, VZV, Epstein-Barr virus, cytomegalovirus), flaviviruses (yellow fever), orthomyxoviruses (influenza), papillomaviruses (cancer), paramyxoviruses (measles, mumps), picornoviruses (rhinovirus, poliovirus, coxsackie-virus), polyomaviruses (BK virus, JC virus), poxviruses (smallpox), reovirus (Colorado tick fever), retroviruses (HIV, HTLV), rhabdoviruses (rabies), rotaviruses (gastroenteritis), and togaviruses (encephalitis, rubella); bacterial infections, fungal infections, parasitic infections, protozoal infections, and helminthic infections; liver disorders, including cirrhosis, jaundice, cholestasis, hereditary hyperbilirubinemia, hepatic encephalopathy, hepatorenal syndrome, hepatitis, hepatic steatosis, hemochromatosis, Wilson's disease, alpha$_1$-antitrypsin deficiency, Reye's syndrome, primary sclerosing cholangitis, liver infarction, portal vein obstruction and thrombosis, passive congestion, centrilobular necrosis, peliosis hepatis, hepatic vein thrombosis, veno-occlusive disease, preeclampsia, eclampsia, acute fatty liver of pregnancy, intrahepatic cholestasis of pregnancy, and hepatic tumors including nodular hyperplasias, adenomas, and carcinomas; and cardiac and skeletal muscle disorders, including cardiomyopathy, myocarditis, Duchenne's muscular dystrophy, Becker's muscular dystrophy, myotonic dystrophy, central core disease, nemaline myopathy, centronuclear myopathy, lipid myopathy, mitochondrial myopathy, infectious myositis, polymyositis, dermatomyositis, inclusion body myositis, thyrotoxic myopathy, and ethanol myopathy.

The polynucleotide sequences encoding HUFA may be used in Southern or northern analysis, dot blot, or other membrane-based technologies; in PCR technologies; in dipstick, pin, and ELISA assays; and in microarrays utilizing fluids or tissues from patient biopsies to detect altered HUFA expression. Such qualitative or quantitative methods are well known in the art.

In a particular aspect, the nucleotide sequences encoding HUFA may be useful in assays that detect the presence of associated disorders, particularly those mentioned above. The nucleotide sequences encoding HUFA may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered from that of a comparable control sample, the nucleotide sequences have hybridized with nucleotide sequences in the sample, and the presence of altered levels of nucleotide sequences encoding HUFA in the sample indicates the presence of the associated disorder. Such assays may also be used to evaluate the efficacy of a particular therapeutic treatment regimen in animal studies, in clinical trials, or in monitoring the treatment of an individual patient.

In order to provide a basis for the diagnosis of a disorder associated with expression of HUFA, a normal or standard profile for expression is established. This may be accomplished by combining body fluids or cell extracts taken from normal subjects, either animal or human, with a sequence, or a fragment thereof, encoding HUFA, under conditions suitable for hybridization or amplification. Standard hybridization may be quantified by comparing the values obtained from normal subjects with values from an experiment in which a known amount of a substantially purified polynucleotide is used. Standard values obtained from normal samples may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to evaluate whether the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HUFA may involve the use of PCR. These oligomers may be chemically synthesized, generated enzymatically, or produced in vitro. Oligomers will preferably contain a fragment of a polynucleotide encoding HUFA, or a fragment of a polynucleotide complementary to the polynucleotide encoding HUFA, and will be employed under optimized conditions for identification of a specific gene or condition. Oligomers may also be employed under less stringent conditions for detection or quantitation of closely related DNA or RNA sequences.

Methods which may also be used to quantitate the expression of HUFA include radiolabeling or biotinylating nucleotides, coamplification of a control nucleic acid, and interpolating results from standard curves. (Melby, P. C. et al. (1993) J. Immunol. Methods 159:235–244, and Duplaa, C. et al. (1993) Anal. Biochem. 212: 229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously (to produce a transcript image) and to identify genetic variants, mutations, and polymorphisms. This information may be used in determining gene function, in understanding the genetic basis of a disorder, in diagnosing a disorder, and in developing and monitoring the activities of therapeutic agents.

In one embodiment, the microarray is prepared and used according to methods known in the art, such as those described in published PCT application WO95/11995 (Chee et al.), Lockhart, D. J. et al. (1996; Nat. Biotech. 14:1675–1680), and Schena, M. et al. (1996; Proc. Natl. Acad. Sci. 93:10614–10619).

The microarray is preferably composed of a large number of unique single-stranded nucleic acid sequences, usually either synthetic antisense oligonucleotides or fragments of cDNAs, fixed to a solid support. The oligonucleotides are preferably about 6 to 60 nucleotides in length, more preferably about 15 to 30 nucleotides in length, and most preferably about 20 to 25 nucleotides in length. For a certain type of microarray, it may be preferable to use oligonucleotides which are about 7 to 10 nucleotides in length. The microarray may contain oligonucleotides which cover the known 5' or 3' sequence, or may contain sequential oligonucleotides which cover the full length sequence or unique oligonucleotides selected from particular areas along the length of the sequence. Polynucleotides used in the microarray may be oligonucleotides specific to a gene or genes of interest in which at least a fragment of the sequence is known or oligonucleotides specific to one or more unidentified cDNAs common to a particular cell or tissue type or to a normal, developmental, or disease state. In certain situations, it may be appropriate to use pairs of oligonucleotides on a microarray. The pairs will be identical, except for one nucleotide preferably located in the center of the sequence. The second oligonucleotide in the pair (mismatched by one) serves as a control. The number of oligonucleotide pairs may range from about 2 to 1,000,000.

In order to produce oligonucleotides to a known sequence for a microarray, the gene of interest is examined using a computer algorithm which starts at the 5' end, or, more preferably, at the 3' end of the nucleotide sequence. The algorithm identifies oligomers of defined length that are unique to the gene, have a GC content within a range suitable for hybridization, and lack predicted secondary structure that may interfere with hybridization. In one aspect, the oligomers are synthesized at designated areas on a substrate using a light-directed chemical process. The substrate may be paper, nylon, any other type of membrane, filter, chip, glass slide, or any other suitable solid support.

In one aspect, the oligonucleotides may be synthesized on the surface of the substrate by using a chemical coupling procedure and an ink jet application apparatus, such as that described in published PCT application WO95/251116 (Baldeschweiler et al.). In another aspect, a grid array analogous to a dot or slot blot (HYBRIDOT apparatus, GIBCO/BRL) may be used to arrange and link cDNA fragments or oligonucleotides to the surface of a substrate using a vacuum system or thermal, UV, mechanical or chemical bonding procedures. In yet another aspect, an array may be produced by hand or by using available devices, materials, and machines (including Brinkmann multichannel pipettors or robotic instruments), and may contain 8, 24, 96, 384, 1536, or 6144 oligonucleotides, or any other multiple from 2 to 1,000,000 which lends itself to the efficient use of commercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce nucleic acid sequences which are complementary to the nucleic acids on the microarray. If the microarray consists of cDNAs, antisense RNAs (aRNA) are appropriate probes. Therefore, in one aspect, mRNA is used to produce cDNA which, in turn and in the presence of fluorescent nucleotides, is used to produce fragment or oligonucleotide aRNA probes. These fluorescently labeled probes are incubated with the microarray so that the probe sequences hybridize to the cDNA oligonucleotides of the microarray. In another aspect, nucleic acid sequences used as probes can include polynucleotides, fragments, and complementary or antisense sequences produced using restriction enzymes, PCR technologies, and Oligolabeling or TransProbe kits (Pharmacia & Upjohn) well known in the area of hybridization technology.

Incubation conditions are adjusted so that hybridization occurs with precise complementary matches or with various degrees of less complementarity. After removal of nonhybridized probes, a scanner is used to determine the levels and patterns of fluorescence. The scanned images are examined to determine the degree of complementarity and the relative abundance of each oligonucleotide sequence on the microarray. A detection system may be used to measure the absence, presence, and amount of hybridization for all of the distinct sequences simultaneously. This data may be used for large scale correlation studies or for functional analysis of the sequences, mutations, variants, or polymorphisms among samples. (Heller, R. A. et al. (1997) Proc. Natl. Acad. Sci. 94:2150–2155.)

In another embodiment of the invention, nucleic acid sequences encoding HUFA may be used to generate hybridization probes useful for mapping the naturally occurring genomic sequence. The sequences may be mapped to a particular chromosome, to a specific region of a chromosome, or to artificial chromosome constructions, such as human artificial chromosomes (HACs), yeast artificial chromosomes (YACs), bacterial artificial chromosomes (BACs), bacterial P1 constructions, or single chromosome cDNA libraries, such as those reviewed in Price, C. M. (1993; Blood Rev. 7:127–134) and Trask, B. J. (1991; Trends Genet. 7:149–154).

Fluorescent in situ hybridization (FISH, as described, e.g., in Heinz-Ulrich, et al. (1995) in Meyers, R. A. (ed.) *Molecular Biology and Biotechnology,* pp. 965–968, VCH Publishers New York, N.Y.) may be correlated with other physical chromosome mapping techniques and genetic map data. Examples of genetic map data can be found in various scientific journals or at the Online Mendelian Inheritance in Man (OMIM) site. Correlation between the location of the gene encoding HUFA on a physical chromosomal map and a specific disorder, or predisposition to a specific disorder, may help define the region of DNA associated with that disorder. The nucleotide sequences of the subject invention may be used to detect differences in gene sequences between normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, ataxia-telangiectasia (AT) to 11 q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc., among normal, carrier, or affected individuals.

In another embodiment of the invention, HUFA, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HUFA and the agent being tested may be measured.

Another technique for drug screening which may be used provides for high throughput screening of compounds having suitable binding affinity to the protein of interest as described in published PCT application WO84/03564 (Geysen, et al.). In this method, large numbers of different small test compounds are synthesized on a solid substrate, such as plastic pins or some other surface. The test compounds are reacted with HUFA, or fragments thereof, and washed. Bound HUFA is then detected by methods well known in the art. Purified HUFA can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HUFA specifically compete with a test compound for binding HUFA. In this manner, antibodies can be used to detect the presence of any peptide which shares one or more antigenic determinants with HUFA.

In additional embodiments, the nucleotide sequences which encode HUFA may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. cDNA Library Construction
BRSTTUT03
The BRSTTUT03 cDNA library was constructed from cancerous breast tissue removed from a 58-year-old Caucasian female who had undergone unilateral extended simple mastectomy following diagnosis of multicentric invasive grade 4 mammary lobular carcinoma.

The frozen tissue was homogenized and lysed using a Polytron PT-3000 homogenizer (Brinkmann Instruments, Westbury, N.J.) in guanidinium isothiocyanate solution. The lysate was centrifuged over a 5.7 M CsCl cushion using an SW28 rotor in an L8-70M ultracentrifuge (Beckman Instruments) for 18 hours at 25,000 rpm at ambient temperature. The RNA was extracted with acid phenol pH 4.0, precipitated using 0.3 M sodium acetate and 2.5 volumes of ethanol, resuspended in RNAse-free water and DNase treated at 37° C. The RNA extraction and precipitation were repeated as before. The mRRNA was then isolated using the OLIGOTER kit (QIAGEN Inc., Chatsworth, Calif.) and used to construct the cDNA library.

The mRNA was handled according to the recommended protocols in the SUPERSCRIPT plasmid system for cDNA synthesis and plasmid cloning (Catalog #18248-013; Gibco/BRL), cDNAs were fractionated on a SEPHAROSE CL4B column (Catalog #275105-01; Pharmacia), and those cDNAs exceeding 400 bp were ligated into PSPORT I. The plasmid PSPORT I was subsequently transformed into DH5α competent cells (Catalog #18258-012; Gibco/BRL).
OVARTUT02
The OVARTUT02 library was constructed from tumorous ovary tissue obtained from a 51-year-old Caucasian female during a total abdominal hysterectomy.

The frozen tissue was homogenized and lysed in TRIZOL reagent (1 g tissue/10 ml TRIZOL; Catalog #10296-028; Gibco/BRL), a monoplastic solution of phenol and guanidine isothiocyanate, using a Polytron PT-3000 homogenizer (Brinkmann Instruments, Westbury, N.Y.). After a brief incubation on ice, chloroform was added (1:5 v/v) and the lysate was centrifuged. The upper chloroform layer was removed to a fresh tube and the RNA extracted with isopropanol, resuspended in DEPC-treated water, and DNase treated for 25 min at 37° C. The RNA was extracted once with acid phenol-chloroform pH 4.7 and precipitated using 0.3M sodium acetate and 2.5 volumes ethanol. The mRNA was then isolated using the OLIGOTEX kit (QIAGEN) and used to construct the cDNA library.

The mRNA was handled according to the recommended protocols in the SUPERSCRIPT plasmid system for cDNA Synthesis and plasmid cloning (Catalog #18248-013, Gibco/BRL).The cDNAs were fractionated on a SEPHAROSE CL4B column (Catalog #275105-01; Pharmacia), and those cDNAs exceeding 400 bp were ligated into pINCY 1 (Incyte). The plasmid pINCY 1 was subsequently transformed into DH5α™ competent cells (Catalog #18258-012; Gibco/BRL).

II. Isolation and Sequencing of cDNA Clones
Plasmid DNA was released from the cells and purified using the R.E.A.L. PREP 96 plasmid kit (Catalog #26173; QIAGEN). This kit enables the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975; J. Mol. Biol. 94:441f), using a MICROLAB 2200 (Hamilton, Reno, Nev.) in combination with Peltier PTC200 thermal cycler (MJ Research, Watertown, Mass.) and Applied Biosystems 377 DNA sequencing systems; and the reading frame was determined.

III. Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool). (Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms such as the one described in Smith, T. et al. (1992; Protein Engineering 5:35–51), could have been used when dealing with primary sequence patterns and secondary structure gap penalties. The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-10}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for homology.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (Sambrook, supra, ch. 7; and Ausubel, supra, ch. 4 and 16.)

Analogous computer techniques applying BLAST are used to search for identical or related molecules in nucleotide databases such as the GenBank or the LIFESEQ database (Incyte Pharmaceuticals). This analysis is much faster than multiple membrane-based hybridizations. In addition, the sensitivity of the computer search can be modified to determine whether any particular match is categorized as exact or homologous.

The basis of the search is the product score, which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding HUFA occurs. Abundance and percent abundance are also reported. Abundance directly reflects the number of times a particular transcript is represented in a cDNA library, and percent abundance is abundance divided by the total number of sequences examined in the cDNA library.

V. Extension of HUFA Encoding Polynucleotides

The nucleic acid sequences of Incyte Clones 1995961 and 2595635 were used to design oligonucleotide primers for extending partial nucleotide sequences to full length. For each nucleic acid sequence, one primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. PCR was performed using the Peltier (PTC200 thermal cycler M.J. Research, Watertown, Mass.), beginning with 40 pmol of each primer and the recommended concentrations of all other components of the kit, with the following parameters:

| Step | Condition |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat steps 4 through 6 for an additional 15 cycles |
| Step 8 | 94° C. for 15 sec |
| Step 9 | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 μl to 10 μl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK (QIAGEN), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2 to 3 hours, or overnight at 16° C. Competent E. coli cells (in 40 μl of appropriate media) were transformed with 3 μl of ligation mixture and cultured in 80 μl of SOC medium. (Sambrook, supra, Appendix A, p. 2.) After incubation for one hour at 37° C., the E. coli mixture was plated on Luria Bertani (LB) agar (Sambrook, supra, Appendix A, p. 1) containing 2x Carb. The following day, several colonies were randomly picked from each plate and cultured in 150 μl of liquid LB/2× Carb medium placed in an individual well of an appropriate commercially-available sterile 96-well plate. The following day, 5 µl of each overnight culture was transferred into a non-sterile 96-well plate and, after dilution 1:10 with water, 5 µl from each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| Step | |
|---|---|
| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NO:2 and SEQ ID NO:4 are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2 and SEQ ID NO:4 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer and 250 µCi of [$\lambda$-$^{32}$P] adenosine triphosphate (Amersham) and T4 polynucleotide kinase (DuPont NEN, Boston, Mass.). The labeled oligonucleotides are substantially purified using a SEPHADEX G-25 superfine resin column (Pharmacia & Upjohn). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba 1, or Pvu II (DuPont NEN).

The DNA from each digest is fractionated on a 0.7 percent agarose gel and transferred to nylon membranes (NYTRAN Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film on other film (Kodak, Rochester, N.Y.) is exposed to the blots or the blots are exposed to a PhosphorImager cassette (Molecular Dynamics, Sunnyvale, Calif.) hybridization patterns are compared visually.

VII. Microarrays

To produce oligonucleotides for a microarray, one of the nucleotide sequences of the present invention is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies approximately 20 sequence-specific oligonucleotides of 20 nucleotides in length (20-mers). A matched set of oligonucleotides are created in which one nucleotide in the center of each sequence is altered. This process is repeated for each gene in the microarray, and double sets of twenty 20-mers are synthesized and arranged on the surface of the silicon chip using a light-directed chemical process, such as that described in Chee (supra).

In the alternative, a chemical coupling procedure and an ink jet device are used to synthesize oligomers on the surface of a substrate. (See Baldeschweiler, supra.) In another alternative, a grid array analogous to a dot or slot blot is used to arrange and link cDNA fragments or oligonucleotides to the surface of a substrate using a vacuum system or thermal, UV, mechanical, or chemical bonding procedures. A typical array may be produced by hand or using available materials and machines and contain grids of 8 dots, 24 dots, 96 dots, 384 dots, 1536 dots, or 6144 dots. After hybridization, the microarray is washed to remove nonhybridized probes, and a scanner is used to determine the levels and patterns of fluorescence. The scanned image is examined to determine the degree of complementarity and the relative abundance/expression level of each oligonucleotide sequence in the microarray.

VIII. Complementary Polynucleotides

Sequences complementary to the HUFA-encoding sequences, or any parts thereof, are used to detect, decrease, or inhibit expression of naturally occurring HUFA. Although use of oligonucleotides comprising from about 15 to 30 base pairs is described, essentially the same procedure is used with smaller or with larger sequence fragments. Appropriate oligonucleotides are designed using OLIGO 4.06 software and the coding sequence of HUFA. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HUFA-encoding transcript.

IX. Expression of HUFA

Expression of HUFA is accomplished by subcloning the cDNAs into appropriate vectors and transforming the vectors into host cells. In this case, the cloning vector is also used to express HUFA in E. coli. This vector contains a promoter for B-galactosidase upstream of the cloning site, followed by sequence containing the amino-terminal Met and the subsequent seven residues of β-galactosidase. Immediately following these eight residues is a bacteriophage promoter useful for transcription and a linker containing a number of unique restriction sites.

Induction of an isolated, transformed bacterial strain with isopropyl beta-D-thiogalactopyranoside (IPTG) using standard methods produces a fusion protein which consists of the first 8 residues of β-galactosidase, about 5 to 15 residues of linker, and the full length protein. The signal residues direct the secretion of HUFA into bacterial growth media which can be used directly in the following assay for activity.

X. Demonstration of HUFA Activity

HUFA-1

HUFA-1 is assayed by measuring the disappearance of 5-phenyl-2,4-pentadienoyl-CoA and NADPH, which absorb at 340 nm. (Nada, M. A. et al. (1994) Lipids 29:517–521.) A solution of 0.2 M potassium phosphate (pH 8), 0.1 mM NADPH, and 25 µM 5-phenyl-2,4,-pentadienoyl-CoA is mixed in an optical cuvette. The assay is started by the addition of sample to the cuvette. The change in absorbance at 340 nm is measured using an ultraviolet spectrophotometer. The amount of HUFA-1 in the sample is proportional to the decrease in absorbance at 340 nm at 25° C.

HUFA-2

HUFA-2 is assayed in a coupled assay measuring the hydration and subsequent dehydrogenation of either a short-chain enoyl-CoA (crotonyl-CoA) or a long-chain enoyl-CoA (trans-2-dodecenoyl-CoA). (Wanders, R. J. A. et al. (1992) Biochem. Biophys. Res. Commun. 188:1139–1145.) The dehydrogenation reaction converts the NAD analog acetylpyridine adenine dinucleotide (APAD) to the reduced form APADH, which absorbs at 365 nm. A solution of 100 mM Tris-HCl (pH 8), 1 mM APAD, 0.1% (w/v) Triton X-100, 7.1 units/ml 3-hydroxyacyl-CoA dehydrogenase from pig heart, and sample is mixed in an optical cuvette and incubated for two minutes at 37° C. Crotonyl-CoA or trans-2-dodecenoyl-CoA at a final concentration of 100 $\mu$M is added to start the reaction. The change in absorbance at 365 nm is measured using an ultraviolet spectrophotometer. The amount of HUFA-2 in the sample is proportional to the increase in absorbance at 365 nm at 37° C.

XI. Production of HUFA Specific Antibodies

HUFA substantially purified using PAGE electrophoresis (Harrington, M. G. (1990) Methods Enzymol. 182:488–495), or other purification techniques, is used to immunize rabbits and to produce antibodies using standard protocols. The HUFA amino acid sequence is analyzed using LASERGENE software (DNASTAR Inc.) to determine regions of high immunogenicity, and a corresponding oligopeptide is synthesized and used to raise antibodies by means known to those of skill in the art. Selection of appropriate epitopes, such as those near the C-terminus or in hydrophilic regions, is described by Ausubel F. M. et al. (1995 and periodic supplements) *Current Protocols in Molecular Biology*, ch. 11, John Wiley & Sons, New York, N.Y. and by others.

Typically, the oligopeptides are 15 residues in length, and are synthesized using an Applied Biosystems peptide synthesizer using fmoc-chemistry and coupled to KLH (Sigma, St. Louis, Mo.) by reaction with N-maleimidobenzoyl-N-hydroxysuccinitride ester (MBS), following the procedure described in Ausubel et al., supra. Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII. Purification of Naturally Occurring HUFA Using Specific Antibodies

Naturally occurring or recombinant HUFA is substantially purified by immunoaffinity chromatography using antibodies specific for HUFA. An immunoaffinity column is constructed by covalently coupling HUFA antibody to an activated chromatographic resin, such as CNBr-activated SEPHAROSE (Pharmacia & Upjohn). After the coupling, the resin is blocked and washed according to the manufacturer's instructions.

Media containing HUFA are passed over the immunoaffinity column, and the column is washed under conditions that allow the preferential absorbance of HUFA (e.g., high ionic strength buffers in the presence of detergent). The column is eluted under conditions that disrupt antibody/HUFA binding (e.g., a buffer of pH 2 to pH 3, or a high concentration of a chaotrope, such as urea or thiocyanate ion), and HUFA is collected.

XIII. Identification of Molecules Which Interact with HUFA

HUFA or biologically active fragments thereof are labeled with $^{125}$I Bolton-Hunter reagent. (Bolton et al. (1973) Biochem. J. 133:529.) Candidate molecules previously arrayed in the wells of a multi-well plate are incubated with the labeled HUFA, washed, and any wells with labeled HUFA complex are assayed. Data obtained using different concentrations of HUFA are used to calculate values for the number, affinity, and association of HUFA with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

---

What is claimed is:

1. An isolated and purified polynucleotide sequence encoding a polypeptide comprising an amino acid sequence selected from the group consisting of SEQ ID NO: 1 and SEQ ID NO:3.

2. A composition comprising the polynucleotide sequence of claim 1.

3. An isolated and purified polynucleotide sequence which hybridizes under stringent conditions of 35° C. in 35% formamide to the polynucleotide sequence of claim 1.

4. An isolated and purified polynucleotide sequence which is complementary to he polynucleotide sequence of claim 1.

5. An isolated and purified polynucleotide sequence comprising a polynucleotide sequence selected from the group consisting of SEQ ID NO:2 and SEQ ID NO:4.

6. An isolated and purified polynucleotide sequence which is complementary to the polynucleotide sequence of claim 5.

7. An expression vector containing the polynucleotide sequence of claim 1.

8. A host cell containing the expression vector of claim 7.

9. A method for producing a polypeptide comprising the amino acid sequence of SEQ ID NO: 1 or SEQ ID NO:3, the method comprising the steps of:
   a) culturing the host cell of claim 8 under conditions suitable for the expression of the polypeptide; and
   b) recovering the polypeptide from the host cell culture.

10. A method for detecting a polynucleotide encoding HUFA in a biological sample containing nucleic acids, the method comprising the steps of:
   (a) hybridizing the polynucleotide of claim 4 to at least one of the nucleic acids in the biological sample, thereby forming a hybridization complex; and
   (b) detecting the hybridization complex, wherein the presence of the hybridization complex correlates with the presence of a polynucleotide encoding HUFA in the biological sample.

11. The method of claim 10 wherein the nucleic acids of the biological sample are amplified by the polymerase chain reaction prior to hybridization.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 303 amino acids
      (B) TYPE: amino acid
      (C) STRANDEDNESS: single
      (D) TOPOLOGY: linear (vii) IMMEDIATE SOURCE:
      (A) LIBRARY: BRSTTUT03
      (B) CLONE: 1995961

(xi) SEQUENCE DESCRIPTION: SEQ ID NO:1:

Met Ala Ser Trp Ala Lys Gly Arg Ser Tyr Leu Ala Pro Gly Leu Leu

```
        1               5                  10                 15
    Gln Gly Gln Val Ala Ile Val Thr Gly Gly Ala Thr Gly Ile Gly Lys
                    20                  25                  30
    Ala Ile Val Lys Glu Leu Leu Glu Leu Gly Ser Asn Val Val Ile Ala
                    35                  40                  45
    Ser Arg Lys Leu Glu Arg Leu Lys Ser Ala Ala Asp Glu Leu Gln Ala
                50                  55                  60
    Asn Leu Pro Pro Thr Lys Gln Ala Arg Val Ile Pro Ile Gln Cys Asn
    65                  70                  75                  80
    Ile Arg Asn Glu Glu Val Asn Asn Leu Val Lys Ser Thr Leu Asp
                    85                  90                  95
    Thr Phe Gly Lys Ile Asn Phe Leu Val Asn Asn Gly Gly Gln Phe
                    100                 105                 110
    Leu Ser Pro Ala Glu His Ile Ser Ser Lys Gly Trp His Ala Val Leu
                115                 120                 125
    Glu Thr Asn Leu Thr Gly Thr Phe Tyr Met Cys Lys Ala Val Tyr Ser
                130                 135                 140
    Ser Trp Met Lys Glu His Gly Gly Ser Ile Val Asn Ile Ile Val Pro
    145                 150                 155                 160
    Thr Lys Ala Gly Phe Pro Leu Ala Val His Ser Gly Ala Ala Arg Ala
                    165                 170                 175
    Gly Val Tyr Asn Leu Thr Lys Ser Leu Ala Leu Glu Trp Ala Cys Ser
                    180                 185                 190
    Gly Ile Arg Ile Asn Cys Val Ala Pro Gly Val Ile Tyr Ser Gln Thr
                    195                 200                 205
    Ala Val Glu Asn Tyr Gly Ser Trp Gly Gln Ser Phe Phe Glu Gly Ser
                210                 215                 220
    Phe Gln Lys Ile Pro Ala Lys Arg Ile Gly Val Pro Glu Glu Val Ser
    225                 230                 235                 240
    Ser Val Val Cys Phe Leu Leu Ser Pro Ala Ala Ser Phe Ile Thr Gly
                    245                 250                 255
    Gln Ser Val Asp Val Asp Gly Gly Arg Ser Leu Tyr Thr His Ser Tyr
                    260                 265                 270
    Glu Val Pro Asp His Asp Asn Trp Pro Lys Gly Ala Gly Asp Leu Ser
                275                 280                 285
    Val Val Lys Lys Met Lys Glu Thr Phe Lys Glu Lys Ala Lys Leu
                290                 295                 300

(2) INFORMATION FOR SEQ ID NO:2:

(i) SEQUENCE CHARACTERISTICS:
        (A) LENGTH: 1210 base pairs
        (B) TYPE: nucleic acid
        (C) STRANDEDNESS: single
        (D) TOPOLOGY: linear (vii) IMMEDIATE SOURCE:
        (A) LIBRARY: BRSTTUT03
        (B) CLONE: 1995961

(xi) SEQUENCE DESCRIPTION: SEQ ID NO:2:

NNCCTGAGAC CCAGAAGGGC CTGCGCTCAG CTGCTCTGGC ACCCCGCTGC AGGGATGGCC    60

TCCTGGGCTA AGGGCAGGAG CTACCTGGCG CCTGGTTTGC TGCAGGGCCA AGTGGCCATC   120

GTCACCGGCG GGGCCACGGG CATCGGAAAA GCCATCGTGA AGGAGCTCCT GGAGCTGGGG   180

AGTAATGTGG TCATTGCATC CCGTAAGTTG GAGAGATTGA AGTCTGCGGC AGATGAACTG   240
```

-continued

```
CAGGCCAACC TACCTCCCAC AAAGCAGGCA CGAGTCATTC CCATACAATG CAACATCCGG    300

AATGAGGAGG AGGTGAATAA TTTGGTCAAA TCTACCTTAG ATACTTTTGG TAAGATCAAT    360

TTCTTGGTGA ACAATGGAGG AGGCCAGTTT CTTTCCCCTG CTGAACACAT CAGTTCTAAG    420

GGATGGCACG CTGTGCTTGA GACCAACCTG ACGGGTACCT TCTACATGTG CAAAGCAGTT    480

TACAGCTCCT GGATGAAAGA GCATGGAGGA TCTATCGTCA ATATCATTGT CCCTACTAAA    540

GCTGGATTTC CATTAGCTGT GCATTCTGGA GCTGCAAGAG CAGGTGTTTA CAACCTCACC    600

AAATCTTTAG CTTTGGAATG GGCCTGCAGT GGAATACGGA TCAATTGTGT TGCCCCTGGA    660

GTTATTTATT CCCAGACTGC TGTGGAGAAC TATGGTTCCT GGGGACAAAG CTTCTTTGAA    720

GGGTCTTTTC AGAAAATCCC CGCTAAACGA ATTGGTGTTC CTGAGGAGGT CTCCTCTGTG    780

GTCTGCTTCC TACTGTCTCC TGCAGCTTCC TTCATCACTG GACAGTCGGT GGATGTGGAT    840

GGGGGCCGGA GTCTCTATAC TCACTCGTAT GAGGTACCAG ATCATGACAA CTGGCCCAAG    900

GGAGCAGGGG ACCTTTCTGT TGTCAAAAAG ATGAAGGAGA CCTTTAAGGA GAAAGCTAAG    960

CTCTGAGCTG AGGAAACAAG GTGTCCTCCA TCCCCCAGTG CCTTCACATC TTGAGGATAT   1020

GCTTCTGTAC TTTTTAAAAG CTTATAGTTG GTATGGAAAA CATTTTTCTT ATTTTTAAGT   1080

GTTATTAATT ATATCTATGG AAAAACTATT CCTGAAATAT ATACAGTCTT ATGTCGCAAT   1140

CAGAGTCTTT TAACCTATGA TTTAAGAATG TATAAGTAAC AGAGATTAAC ATATTTTAAT   1200

GACTTTACTC                                                         1210
```

(2) INFORMATION FOR SEQ ID NO:3:

(i) SEQUENCE CHARACTERISTICS:
        (A) LENGTH: 301 amino acids
        (B) TYPE: amino acid
        (C) STRANDEDNESS: single
        (D) TOPOLOGY: linear (vii) IMMEDIATE SOURCE:
        (A) LIBRARY: OVARTUT02
        (B) CLONE: 2595635

(xi) SEQUENCE DESCRIPTION: SEQ ID NO:3:

```
Met Ala Lys Ser Leu Leu Lys Thr Ala Ser Leu Ser Gly Arg Thr Lys
 1               5                  10                  15

Leu Leu His Gln Thr Gly Leu Ser Leu Tyr Ser Thr Ser His Gly Phe
                20                  25                  30

Tyr Glu Glu Val Lys Lys Thr Leu Gln Gln Phe Pro Gly Gly Ser
            35                  40                  45

Ile Asp Leu Gln Lys Glu Asp Asn Gly Ile Gly Ile Leu Thr Leu Asn
        50                  55                  60

Asn Pro Ser Arg Met Asn Ala Phe Ser Gly Val Met Met Leu Gln Leu
65                  70                  75                  80

Leu Glu Lys Val Ile Glu Leu Glu Asn Trp Thr Glu Gly Lys Gly Leu
                85                  90                  95

Ile Val Arg Gly Ala Lys Asn Thr Phe Ser Ser Gly Ser Asp Leu Asn
            100                 105                 110

Ala Val Lys Ser Leu Gly Thr Pro Glu Asp Gly Met Ala Val Cys Met
        115                 120                 125

Phe Met Gln Asn Thr Leu Thr Arg Phe Met Arg Leu Pro Leu Ile Ser
    130                 135                 140

Val Ala Leu Val Gln Gly Trp Ala Leu Gly Gly Gly Ala Glu Phe Thr
145                 150                 155                 160
```

-continued

```
Thr Ala Cys Asp Phe Arg Leu Met Thr Pro Glu Ser Lys Ile Arg Phe
                165                 170                 175
Val His Lys Glu Met Gly Ile Ile Pro Ser Trp Gly Gly Thr Thr Arg
            180                 185                 190
Leu Val Glu Ile Ile Gly Ser Arg Gln Ala Leu Lys Val Leu Ser Gly
        195                 200                 205
Ala Leu Lys Leu Asp Ser Lys Asn Ala Leu Asn Ile Gly Met Val Glu
    210                 215                 220
Glu Val Leu Gln Ser Ser Asp Glu Thr Lys Ser Leu Glu Glu Ala Gln
225                 230                 235                 240
Glu Trp Leu Lys Gln Phe Ile Gln Gly Pro Pro Glu Val Ile Arg Ala
                245                 250                 255
Leu Lys Lys Ser Val Cys Ser Gly Arg Glu Leu Tyr Leu Glu Glu Ala
            260                 265                 270
Leu Gln Asn Glu Arg Asp Leu Leu Gly Thr Val Trp Gly Gly Pro Ala
        275                 280                 285
Asn Leu Glu Ala Ile Ala Lys Lys Gly Lys Phe Asn Lys
    290                 295                 300
```

(2) INFORMATION FOR SEQ ID NO:4:

(i) SEQUENCE CHARACTERISTICS:
    (A) LENGTH: 2714 base pairs
    (B) TYPE: nucleic acid
    (C) STRANDEDNESS: single
    (D) TOPOLOGY: linear (vii) IMMEDIATE SOURCE:
    (A) LIBRARY: OVARTUT02
    (B) CLONE: 2595635

(xi) SEQUENCE DESCRIPTION: SEQ ID NO:4:

```
NAAGCACTTC CTGTCTGCGG CATACAAAAT GTATGGCACG GAATTTTAAG CTTACTGAGC    60
TTTATAAACA CGTCACATTC ACACATTCAA GACACACACT GGATATTCGG ATAAAAACAA   120
ACAAACAAAA AACAGGCTAA ATACCCATTC CCCTCAATAA CTTGGATAAG ATACCTAAAA   180
AAGGTCGACT TCGGTACCTT TCTGTCTTCT CCCCTCTCGC TATTTGCCTA CACTGGCTTC   240
CTCACCTCCA CTTTTTCTCA CGTTTATCTG AGCGAAAACA AGCACGGTTC GGCAGCCTCC   300
TTTCCCAGCC CTACCTTTGT GCTGCAAAAG CGAAAATTCA AAAGCCAAGT ACAATAGGAG   360
ACCGCCCACC CTGGCTCCCT CGTGACACGA GGGAGCGCGA AGCGGAGGGC GCCTCGCGGC   420
AGGAGCGGGA TTTCCGGGGT CACGGGAACC GGCAGGGGAA CGGGATAAAG TTCCTGGAGA   480
AAGGAAAGGA GAGCGTGGGA TAGTAAAAGA GAAGACGCGG AGAAGAGGAG AGGACCTACA   540
AGAACGGAGG ACAGGGGCGC ACGATGGTCC CGGGGGGAGC GGAAACAAAG GCACGCAAAA   600
CGGAAAAGCG TGTGTAGGGG AGCGGAAAAG GAAGTCACCA CCGTGGCCTG CGACGAAATG   660
GCGAAAAGTC TTTTGAAGAC AGCCTCTCTG TCTGGAAGGA CAAAATTGCT ACATCAAACA   720
GGATTGTCAC TTTATAGTAC ATCCCATGGA TTTTATGAGG AAGAAGTGAA AAAAACACTT   780
CAGCAGTTTC CTGGTGGATC CATTGACCTT CAGAAGGAAG ACAATGGCAT TGGCATTCTT   840
ACTCTGAACA ATCCAAGTAG AATGAATGCC TTTTCAGGTG TTATGATGCT ACAACTTCTG   900
GAAAAAGTAA TTGAATTGGA AAATTGGACA GAGGGGAAAG GCCTCATTGT CCGTGGGGCA   960
AAAAATACTT TCTCTTCAGG ATCTGATCTG AATGCTGTGA ATCACTAGG AACTCCAGAG  1020
GATGGAATGG CCGTATGCAT GTTCATGCAA ACACCTTAA CAAGATTTAT GAGACTTCCT  1080
TTAATAAGTG TTGCGCTGGT TCAAGGTTGG GCATTGGGTG GAGGAGCAGA ATTTACTACA  1140
```

```
GCATGTGATT TCAGGTTAAT GACTCCAGAG AGTAAGATCA GATTCGTCCA CAAAGAGATG   1200

GGCATAATAC CAAGCTGGGG TGGCACCACC CGGCTAGTTG AAATAATCGG AAGTAGACAA   1260

GCTCTCAAAG TGTTGAGTGG GGCCCTTAAA CTGGATTCAA AAAATGCTCT AAACATAGGA   1320

ATGGTTGAAG AGGTCTTGCA GTCTTCAGAT GAAACTAAAT CTCTAGAAGA GGCACAAGAA   1380

TGGCTAAAGC AATTCATCCA AGGGCCACCG GAAGTAATTA GAGCTTTGAA AAAATCTGTT   1440

TGTTCAGGCA GAGAGCTATA TTTGGAGGAA GCATTACAGA ACGAAAGAGA TCTTTTAGGA   1500

ACAGTTTGGG GTGGGCCTGC AAATTTAGAG GCTATTGCTA AGAAAGGAAA ATTTAATAAA   1560

TAATTGGTTT TTCGTGTGGA TGTACTCCAA GTAAAGCTCC AGTGACTAAT ATGTATAAAT   1620

GTTAAATGAT ATTAAATATG AACATCAGAA TTACTTTGAA GGCTACTATT AATATGCAGA   1680

CTTACTTTTA ATCATTTGAA TATCTGAACT CATTTACCTC ATTTCTTGCC AATTACTCAC   1740

TTGGGTATTT ACTGCGTAAT CTGGAACATT TAGCTAAAAT ATACACTTTT GGCTTAAAAA   1800

TTATTGCTGT CAATTCCAAT AATAATTCTT AGCTTATAAC CAAAGAGCAG TGTTTAAAAG   1860

GAGAGCTTCT ATACAAAACC TATTCCTGGC GTTACTTTTC ATACAATTTT GTTCTGTTT    1920

TACCTGGAAA TAATTTACCA AAATAACTGA GTGTTGCTGC TAAAGAACAA AAGTGGGGAG   1980

GTATCAGGGA ACAAGAAAAC AAGAAAGGGT ATGATCAATC ATTTCTTCT GCTCCAAACA    2040

GCTGGAGTAA AATTCATGGG AAATGGCCCT TCATTTAAAA AAAGATGTAC CTCACTACCC   2100

ACTACAAATT TGGAACTTTG TTCTTTTCAA TAATTAGTTT TCTATTGTAA ATTACCTACT   2160

AAACAGTGGT AGCCATGACA TGGAAAGTCA ACTGATTCTA CAATTGGACA TTCATTTGTG   2220

TGCCCTGGAA TTTCAACTA GTAATAAACA ACTACTGTTG ATGTAGTTTT AAACCACTTG    2280

AAGGGACTCA TGAAGCATCC TGCAACATAA ATTTGCATTT TTACATCAGA TTTCTTTTTT   2340

TTCCTGAAAA ACAACTAACC TTCTAACAAC TATCTTTCAA AAGTAAATGT AATAAAAATG   2400

CACAACATAA AATGTTTATG ATCCCAGCAA TACACTTTTT AAAAAATGTG AAAGTCAAAG   2460

AATTAAGTTC TAGTTCTGAC TCATCACAAG AGGTCAAAAG TATTTGCTAC TGTAACATTC   2520

AATTCACATT TGAGAATCAT GGTAAAAATA ACTTGTATTT GCCTTACCAT CATGATCCTA   2580

CTGTTGAGTT AGGAAAATAT GGTTAGACAG ACTCACATTA CTTTTTTTCA GAGGTAAACT   2640

CTAGATTACT GTGTCAACCC AATACTATTT GGCCATAGAT GTAAAAACTA CCAAATAAAA   2700

GTGGATTTTG TGTC                                                    2714

(2) INFORMATION FOR SEQ ID NO:5:

(i) SEQUENCE CHARACTERISTICS:
        (A) LENGTH: 295 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 730864

(xi) SEQUENCE DESCRIPTION: SEQ ID NO:5:

Met Asp Thr Met Asn Thr Ala Asn Thr Leu Asp Gly Lys Phe Val Thr
 1               5                  10                  15

Glu Gly Ser Trp Arg Pro Asp Leu Phe Lys Gly Lys Val Ala Phe Val
            20                  25                  30

Thr Gly Gly Ala Gly Thr Ile Cys Arg Val Gln Thr Glu Ala Leu Val
        35                  40                  45
```

```
Leu Leu Gly Cys Lys Ala Ala Ile Val Gly Arg Asp Gln Glu Arg Thr
    50                  55                  60

Glu Gln Ala Ala Lys Gly Ile Ser Gln Leu Ala Lys Asp Lys Asp Ala
65                  70                  75                  80

Val Leu Ala Ile Ala Asn Val Asp Val Arg Asn Phe Glu Gln Val Glu
                    85                  90                  95

Asn Ala Val Lys Lys Thr Val Glu Lys Phe Gly Lys Ile Asp Phe Val
                100                 105                 110

Ile Ala Gly Ala Ala Gly Asn Phe Val Cys Asp Phe Ala Asn Leu Ser
            115                 120                 125

Pro Asn Ala Phe Lys Ser Val Val Asp Ile Asp Leu Leu Gly Ser Phe
        130                 135                 140

Asn Thr Ala Lys Ala Cys Leu Lys Glu Leu Lys Lys Ser Lys Gly Ser
145                 150                 155                 160

Ile Leu Phe Val Ser Ala Thr Phe His Tyr Tyr Gly Val Pro Phe Gln
                165                 170                 175

Gly His Val Gly Ala Ala Lys Ala Gly Ile Asp Ala Leu Ala Lys Asn
            180                 185                 190

Leu Ala Val Glu Leu Gly Pro Leu Gly Ile Arg Ser Asn Cys Ile Ala
        195                 200                 205

Pro Gly Ala Ile Asp Asn Thr Glu Gly Leu Lys Arg Leu Ala Gly Lys
    210                 215                 220

Lys Tyr Lys Glu Lys Ala Leu Ala Lys Ile Pro Leu Gln Arg Leu Gly
225                 230                 235                 240

Ser Thr Arg Asp Ile Ala Glu Ser Thr Val Tyr Ile Phe Ser Pro Ala
                245                 250                 255

Ala Ser Tyr Val Thr Gly Thr Val Leu Val Asp Gly Gly Met Trp
            260                 265                 270

His Leu Gly Thr Tyr Phe Gly His Glu Leu Tyr Pro Glu Ala Leu Ile
        275                 280                 285

Lys Ser Met Thr Ser Lys Leu
    290                 295

(2) INFORMATION FOR SEQ ID NO:6:

(i) SEQUENCE CHARACTERISTICS:
        (A) LENGTH: 335 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 602703

(xi) SEQUENCE DESCRIPTION: SEQ ID NO:6:

Met Lys Leu Pro Ala Arg Val Phe Phe Thr Leu Gly Ser Arg Leu Pro
1               5                   10                  15

Cys Gly Leu Ala Pro Arg Arg Phe Phe Ser Tyr Gly Thr Lys Ile Leu
                20                  25                  30

Tyr Gln Asn Thr Glu Ala Leu Gln Ser Lys Phe Phe Ser Pro Leu Gln
            35                  40                  45

Lys Ala Met Leu Pro Pro Asn Ser Phe Gln Gly Lys Val Ala Phe Ile
        50                  55                  60

Thr Gly Gly Gly Thr Gly Leu Gly Lys Gly Met Thr Thr Leu Leu Ser
65                  70                  75                  80

Ser Leu Gly Ala Gln Cys Val Ile Ala Ser Arg Lys Met Asp Val Leu
```

85                  90                  95

Lys Ala Thr Ala Glu Gln Ile Ser Ser Gln Thr Gly Asn Lys Val His
                    100                 105                 110

Ala Ile Gln Cys Asp Val Arg Asp Pro Asp Met Val Gln Asn Thr Val
                115                 120                 125

Ser Glu Leu Ile Lys Val Ala Gly His Pro Asn Ile Val Ile Asn Asn
            130                 135                 140

Ala Ala Gly Asn Phe Ile Ser Pro Thr Glu Arg Leu Ser Pro Asn Ala
145                 150                 155                 160

Trp Lys Thr Ile Thr Asp Ile Val Leu Asn Gly Thr Ala Phe Val Thr
                165                 170                 175

Leu Glu Ile Gly Lys Gln Leu Ile Lys Ala Gln Lys Gly Ala Ala Phe
                180                 185                 190

Leu Ser Ile Thr Thr Ile Tyr Ala Glu Thr Gly Ser Gly Phe Val Val
                195                 200                 205

Pro Ser Ala Ser Ala Lys Ala Gly Val Glu Ala Met Ser Lys Ser Leu
            210                 215                 220

Ala Ala Glu Trp Gly Lys Tyr Gly Met Arg Phe Asn Val Ile Gln Pro
225                 230                 235                 240

Gly Pro Ile Lys Thr Lys Gly Ala Phe Ser Arg Leu Asp Pro Thr Gly
                245                 250                 255

Thr Phe Glu Lys Glu Met Ile Gly Arg Ile Pro Cys Gly Arg Leu Gly
                260                 265                 270

Thr Val Glu Glu Leu Ala Asn Leu Ala Ala Phe Leu Cys Ser Asp Tyr
            275                 280                 285

Ala Ser Trp Ile Asn Gly Ala Val Ile Lys Phe Asp Gly Gly Glu Glu
            290                 295                 300

Val Leu Ile Ser Gly Glu Phe Asn Asp Leu Arg Lys Val Thr Lys Glu
305                 310                 315                 320

Gln Trp Asp Thr Ile Glu Glu Leu Ile Arg Lys Thr Lys Gly Ser
                325                 330                 335

(2) INFORMATION FOR SEQ ID NO:7:

(i) SEQUENCE CHARACTERISTICS:
        (A) LENGTH: 335 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 111287

(xi) SEQUENCE DESCRIPTION: SEQ ID NO:7:

Met Ala Leu Leu Ala Arg Ala Phe Phe Ala Gly Val Ser Arg Leu Pro
1               5                   10                  15

Cys Asp Pro Gly Pro Gln Arg Phe Ser Phe Gly Thr Lys Thr Leu
                20                  25                  30

Tyr Gln Ser Ile Asp Ala Pro Gln Ser Lys Phe Phe Pro Pro Ile Leu
            35                  40                  45

Lys Pro Met Leu Pro Pro Asn Ala Phe Gln Gly Lys Val Ala Phe Ile
        50                  55                  60

Thr Gly Gly Gly Thr Gly Leu Gly Lys Ala Met Thr Thr Phe Leu Ser
65                  70                  75                  80

Ser Leu Gly Ala Gln Cys Val Ile Ala Ser Arg Asn Ile Asp Val Leu
                85                  90                  95

```
Lys Ala Thr Ala Glu Glu Ile Thr Ser Lys Thr Gly Asn Lys Val Tyr
                100                 105                 110

Ala Ile Arg Cys Asp Val Arg Asp Pro Asp Met Val His Asn Thr Val
            115                 120                 125

Leu Glu Leu Ile Lys Val Ala Gly His Pro Asp Val Val Ile Asn Asn
        130                 135                 140

Ala Ala Gly Asn Phe Ile Ser Pro Ser Glu Arg Leu Ser Pro Asn Gly
145                 150                 155                 160

Trp Lys Thr Ile Thr Asp Ile Val Leu Asn Gly Thr Ala Tyr Val Thr
                165                 170                 175

Ile Glu Ile Gly Lys Gln Leu Ile Lys Ala Gln Lys Gly Ala Ala Phe
                180                 185                 190

Leu Ala Ile Thr Thr Ile Tyr Ala Glu Ser Gly Ser Gly Phe Val Met
            195                 200                 205

Pro Ser Ser Ser Ala Lys Ser Gly Val Glu Ala Met Asn Lys Ser Leu
        210                 215                 220

Ala Ala Glu Trp Gly Arg Tyr Gly Met Arg Phe Asn Ile Ile Gln Pro
225                 230                 235                 240

Gly Pro Ile Lys Thr Lys Gly Ala Phe Ser Arg Leu Asp Pro Thr Gly
                245                 250                 255

Lys Phe Glu Lys Asp Met Ile Glu Arg Ile Pro Cys Gly Arg Leu Gly
                260                 265                 270

Thr Val Glu Glu Leu Ala Asn Leu Ala Thr Phe Leu Cys Ser Asp Tyr
            275                 280                 285

Ala Ser Trp Ile Asn Gly Ala Val Ile Arg Phe Asp Gly Gly Glu Glu
        290                 295                 300

Val Phe Leu Ser Gly Glu Phe Asn Ser Leu Lys Lys Val Thr Lys Glu
305                 310                 315                 320

Glu Trp Asp Val Ile Glu Gly Leu Ile Arg Lys Thr Lys Gly Ser
                325                 330                 335

(2) INFORMATION FOR SEQ ID NO:8:

(i) SEQUENCE CHARACTERISTICS:
        (A) LENGTH: 339 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 780241

(xi) SEQUENCE DESCRIPTION: SEQ ID NO:8:

Met Ala Ala Val Ala Ala Ala Pro Gly Ala Leu Gly Ser Leu His
1               5                   10                  15

Ala Gly Gly Ala Arg Leu Val Ala Cys Ser Ala Trp Leu Cys Pro
            20                  25                  30

Gly Leu Arg Leu Pro Gly Ser Leu Ala Gly Arg Arg Ala Gly Pro Ala
                35                  40                  45

Ile Trp Ala Gln Gly Trp Val Pro Ala Ala Gly Gly Pro Ala Pro Lys
    50                  55                  60

Arg Gly Tyr Ser Ser Glu Met Lys Thr Glu Asp Glu Leu Arg Val Arg
65                  70                  75                  80

His Leu Glu Glu Glu Asn Arg Gly Ile Val Val Leu Gly Ile Asn Arg
                85                  90                  95
```

```
Ala Tyr Gly Lys Asn Ser Leu Ser Lys Asn Leu Ile Lys Met Leu Ser
            100                 105                 110

Lys Ala Val Asp Ala Leu Lys Ser Asp Lys Val Arg Thr Ile Ile
        115                 120                 125

Ile Arg Ser Glu Val Pro Gly Ile Phe Cys Ala Gly Ala Asp Leu Lys
    130                 135                 140

Glu Arg Ala Lys Met Ser Ser Ser Glu Val Gly Pro Phe Val Ser Lys
145                 150                 155                 160

Ile Arg Ala Val Ile Asn Asp Ile Ala Asn Leu Pro Val Pro Thr Ile
                165                 170                 175

Ala Ala Ile Asp Gly Leu Ala Leu Gly Gly Gly Leu Glu Leu Ala Leu
            180                 185                 190

Ala Cys Asp Ile Arg Val Ala Ala Ser Ser Ala Lys Met Gly Leu Val
            195                 200                 205

Glu Thr Lys Leu Ala Ile Ile Pro Gly Gly Gly Gly Thr Gln Arg Leu
    210                 215                 220

Pro Arg Ala Ile Gly Met Ser Leu Ala Lys Glu Leu Ile Phe Ser Ala
225                 230                 235                 240

Arg Val Leu Asp Gly Lys Glu Ala Lys Ala Val Gly Leu Ile Ser His
                245                 250                 255

Val Leu Glu Gln Asn Gln Gly Asp Ala Ala Tyr Arg Lys Ala Leu
            260                 265                 270

Asp Leu Ala Arg Glu Phe Leu Pro Gln Gly Pro Val Ala Met Arg Val
    275                 280                 285

Ala Lys Leu Ala Ile Asn Gln Gly Met Glu Val Asp Leu Val Thr Gly
290                 295                 300

Leu Ala Ile Glu Glu Ala Cys Tyr Ala Gln Thr Ile Pro Thr Lys Asp
305                 310                 315                 320

Arg Leu Glu Gly Leu Leu Ala Phe Lys Glu Lys Arg Pro Pro Arg Tyr
                325                 330                 335

Lys Gly Glu (2) INFORMATION FOR SEQ ID NO:9:

(i) SEQUENCE CHARACTERISTICS:
        (A) LENGTH: 290 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1922287

(xi) SEQUENCE DESCRIPTION: SEQ ID NO:9:

Met Ala Ala Leu Arg Val Leu Leu Ser Cys Ala Arg Gly Pro Leu Arg
1               5                   10                  15

Pro Pro Val Arg Cys Pro Ala Trp Arg Pro Phe Ala Ser Gly Ala Asn
            20                  25                  30

Phe Glu Tyr Ile Ile Ala Glu Lys Arg Gly Lys Asn Asn Thr Val Gly
        35                  40                  45

Leu Ile Gln Leu Asn Arg Pro Lys Ala Leu Asn Ala Leu Cys Asp Gly
    50                  55                  60

Leu Ile Asp Glu Leu Asn Gln Ala Leu Lys Ile Phe Glu Glu Asp Pro
65              70                  75                  80

Ala Val Gly Ala Ile Val Leu Thr Gly Gly Asp Lys Ala Phe Ala Ala
                85                  90                  95
```

-continued

```
Gly Ala Asp Ile Lys Glu Met Gln Asn Leu Ser Phe Gln Asp Cys Tyr
            100                 105                 110

Ser Ser Lys Phe Leu Lys His Trp Asp His Leu Thr Gln Val Lys Lys
        115                 120                 125

Pro Val Ile Ala Ala Val Asn Gly Tyr Ala Phe Gly Gly Gly Cys Glu
    130                 135                 140

Leu Ala Met Met Cys Asp Ile Ile Tyr Ala Gly Glu Lys Ala Gln Phe
145                 150                 155                 160

Ala Gln Pro Glu Ile Leu Ile Gly Thr Ile Pro Ala Gly Gly Gly Thr
                165                 170                 175

Gln Arg Leu Thr Arg Ala Val Gly Lys Ser Leu Ala Met Glu Met Val
            180                 185                 190

Leu Thr Gly Asp Arg Ile Ser Ala Gln Asp Ala Lys Gln Ala Gly Leu
        195                 200                 205

Val Ser Lys Ile Cys Pro Val Glu Thr Leu Val Glu Glu Ala Ile Gln
    210                 215                 220

Cys Ala Glu Lys Ile Ala Ser Asn Ser Lys Ile Val Val Ala Met Ala
225                 230                 235                 240

Lys Glu Ser Val Asn Ala Ala Phe Glu Met Thr Leu Thr Glu Gly Ser
                245                 250                 255

Lys Leu Glu Lys Lys Leu Phe Tyr Ser Thr Phe Ala Thr Asp Asp Arg
            260                 265                 270

Lys Glu Gly Met Thr Ala Phe Val Gly Lys Arg Lys Ala Asn Phe Lys
        275                 280                 285

Asp Gln
    290

(2) INFORMATION FOR SEQ ID NO:10:

(i) SEQUENCE CHARACTERISTICS:
           (A) LENGTH: 328 amino acids
           (B) TYPE: amino acid
           (C) STRANDEDNESS: single
           (D) TOPOLOGY: linear (vii) IMMEDIATE SOURCE:
           (A) LIBRARY: GenBank
           (B) CLONE: 564065

(xi) SEQUENCE DESCRIPTION: SEQ ID NO:10:

Met Ala Ala Gly Ile Val Ala Ser Arg Arg Leu Arg Asp Leu Leu Thr
1               5                   10                  15

Arg Arg Leu Thr Gly Ser Asn Tyr Pro Gly Leu Ser Ile Ser Leu Arg
            20                  25                  30

Leu Thr Gly Ser Ser Ala Gln Glu Glu Ala Ser Gly Val Ala Leu Gly
        35                  40                  45

Glu Ala Pro Asp His Ser Tyr Glu Ser Leu Arg Val Thr Ser Ala Gln
    50                  55                  60

Lys His Val Leu His Val Gln Leu Asn Arg Pro Asn Lys Arg Asn Ala
65                  70                  75                  80

Met Asn Lys Val Phe Trp Arg Glu Met Val Glu Cys Phe Asn Lys Ile
                85                  90                  95

Ser Arg Asp Ala Asp Cys Arg Ala Val Val Ile Ser Gly Ala Gly Lys
            100                 105                 110

Met Phe Thr Ala Gly Ile Asp Leu Met Asp Met Ala Ser Asp Ile Leu
        115                 120                 125
```

-continued

```
Gln Pro Lys Gly Asp Asp Val Ala Arg Ile Ser Trp Tyr Leu Arg Asp
    130                 135                 140

Ile Ile Thr Arg Tyr Gln Glu Thr Phe Asn Val Ile Glu Arg Cys Pro
145                 150                 155                 160

Lys Pro Val Ile Ala Ala Val His Gly Gly Cys Ile Gly Gly Gly Val
                165                 170                 175

Asp Leu Val Thr Ala Cys Asp Ile Arg Tyr Cys Ala Gln Asp Ala Phe
                180                 185                 190

Phe Gln Val Lys Glu Val Asp Val Gly Leu Ala Ala Asp Val Gly Thr
            195                 200                 205

Leu Glu Arg Leu Pro Lys Val Ile Gly Asn Gln Ser Leu Val Asn Glu
        210                 215                 220

Leu Ala Phe Thr Ala His Lys Met Met Ala Asp Glu Ala Leu Asp Ser
225                 230                 235                 240

Gly Leu Val Ser Arg Val Phe Pro Asp Lys Glu Val Met Leu Asp Ala
                245                 250                 255

Ala Leu Pro Leu Ala Pro Glu Ile Ser Ser Lys Thr Thr Val Leu Val
                260                 265                 270

Gln Ser Thr Lys Val Asn Leu Leu Tyr Ser Arg Asp His Ser Val Ala
        275                 280                 285

Glu Ser Leu Asn Tyr Val Ala Ser Trp Asn Met Ser Met Leu Gln Thr
    290                 295                 300

Gln Asp Leu Val Lys Ser Val Gln Pro Thr Thr Glu Asn Lys Glu Leu
305                 310                 315                 320

Lys Thr Val Thr Phe Ser Lys Leu
                325
```